United States Patent
Chen et al.

(10) Patent No.: US 11,382,354 B2
(45) Date of Patent: Jul. 12, 2022

(54) VAPORIZATION DEVICE HAVING AIR INLET AND OUTLET CHANNELS STRUCTURES

(71) Applicant: SHENZHEN RELX TECHNOLOGY CO., LTD., Shenzhen (CN)

(72) Inventors: Chen Chen, Shenzhen (CN); Yao Fu, Shenzhen (CN); Shuting Feng, Shenzhen (CN); Zugang Yang, Shenzhen (CN); Jin Zhang, Shenzhen (CN)

(73) Assignee: SHENZHEN RELX TECHNOLOGY CO., LTD., Shenzhen (CN)

( * ) Notice: Subject to any disclaimer, the term of this patent is extended or adjusted under 35 U.S.C. 154(b) by 104 days.

(21) Appl. No.: 16/618,801

(22) PCT Filed: Jun. 27, 2019

(86) PCT No.: PCT/CN2019/093231
§ 371 (c)(1),
(2) Date: Dec. 3, 2019

(87) PCT Pub. No.: WO2020/034774
PCT Pub. Date: Feb. 20, 2020

(65) Prior Publication Data
US 2020/0315250 A1    Oct. 8, 2020

(30) Foreign Application Priority Data

Aug. 17, 2018 (CN) .......................... 201810941894.2
Aug. 17, 2018 (CN) .......................... 201810942876.6
(Continued)

(51) Int. Cl.
A24F 40/42    (2020.01)
A61M 11/04    (2006.01)
(Continued)

(52) U.S. Cl.
CPC .............. *A24F 40/42* (2020.01); *A24F 40/10* (2020.01); *A24F 40/46* (2020.01); *A24F 40/48* (2020.01);
(Continued)

(58) Field of Classification Search
CPC .......... A24F 40/42; A24F 40/10; A24F 40/40; A24F 40/46; A24F 40/48
(Continued)

(56) References Cited

U.S. PATENT DOCUMENTS 9,750,284 B2 * 9/2017 Rado ...................... F22B 1/284
2016/0183596 A1 * 6/2016 Rado ...................... A24F 40/44
392/395
(Continued)

FOREIGN PATENT DOCUMENTS

CA    2752255 A1    8/2010
CN    102387719 A    3/2012
(Continued)

OTHER PUBLICATIONS

Office Action of corresponding China patent application No. 201980003520.9 dated May 7, 2022.

*Primary Examiner* — Hae Moon Hyeon
(74) *Attorney, Agent, or Firm* — Idea Intellectual Limited; Margaret A. Burke; Sam T. Yip

(57) ABSTRACT

This application relates to an vaporization device and a method thereof. The provided vaporization device includes a cartridge and a body. The cartridge has a housing, a heating component and a heating component base. The housing and the heating component base define an air inlet channel and an air outlet channel, and the heating component and the heating component base define a cavity. The air inlet channel is in communication with the cavity through a first communication portion, and the first communication portion is
(Continued)

located between the heating component and the heating component base. The air outlet channel is in communication with the cavity through a second communication portion, and the second communication portion is located between the heating component and the heating component base. The body has an accommodation portion. When the cartridge and the body are removably combined, the accommodation portion covers a portion of the cartridge.

19 Claims, 13 Drawing Sheets

(30) Foreign Application Priority Data

Aug. 17, 2018 (CN) .......................... 201810943496.4
Jan. 11, 2019 (CN) .......................... 201910028649.7

(51) Int. Cl.
*A61M 15/00* (2006.01)
*A24F 40/10* (2020.01)
*A24F 40/46* (2020.01)
*A24F 40/51* (2020.01)
*A24F 40/57* (2020.01)
*A24F 40/48* (2020.01)
*A24F 40/53* (2020.01)

(52) U.S. Cl.
CPC .............. *A24F 40/51* (2020.01); *A24F 40/53* (2020.01); *A24F 40/57* (2020.01); *A61M 11/042* (2014.02); *A61M 15/0001* (2014.02)

(58) Field of Classification Search
USPC .................................................. 131/328, 329
See application file for complete search history.

(56) References Cited

U.S. PATENT DOCUMENTS

| | | | |
|---|---|---|---|
| 2019/0208825 A1* | 7/2019 | Qiu | ........................ A24F 40/485 |
| 2020/0367564 A1* | 11/2020 | Li | ............................ A24F 40/44 |

FOREIGN PATENT DOCUMENTS

| | | | | |
|---|---|---|---|---|
| CN | 204232300 U | | 4/2015 | |
| CN | 105192895 A | | 12/2015 | |
| CN | 106418709 A | * | 2/2017 | ........... A24F 40/485 |
| CN | 205962838 U | | 2/2017 | |
| CN | 206260849 U | | 6/2017 | |
| CN | 206453243 U | | 9/2017 | |
| CN | 206776743 U | | 12/2017 | |
| CN | 107865462 A | | 4/2018 | |
| CN | 108185536 A | * | 6/2018 | ............. C04B 35/00 |
| CN | 208863588 U | | 5/2019 | |
| CN | 208987818 U | | 6/2019 | |
| CN | 208987819 U | | 6/2019 | |
| EP | 3753425 A1 | * | 12/2020 | ............. A24F 40/44 |
| EP | 3753427 A1 | * | 12/2020 | ........... H05B 1/0297 |
| EP | 3753428 A1 | * | 12/2020 | ............. A24F 40/42 |
| KR | 20120008751 U | | 12/2012 | |
| WO | 2015120588 A1 | | 8/2015 | |
| WO | WO-2018054388 A1 | * | 3/2018 | ............. A24F 40/50 |

* cited by examiner

VAPORIZATION DEVICE HAVING AIR INLET AND OUTLET CHANNELS STRUCTURES

BACKGROUND OF THE INVENTION

1. Field of the Invention

The present invention relates to a vaporization device and a method thereof, and more particularly to an electronic device providing an inhalable aerosol and a method thereof.

2. Description of the Related Art

An electronic cigarette is an electronic product that heats a vaporizable solution and vaporizes the solution to produce an aerosol for a user to smoke.

In recent years, major manufacturers begin to produce various electronic cigarette products. Generally, an electronic cigarette product includes a housing, an e-liquid storage chamber, an vaporization chamber, a heating component, an air inlet, an airflow channel, an air outlet, a power supply device, a sensing device and a control device. The e-liquid storage chamber is configured to store a vaporizable solution, and the heating component is used to heat and vaporize the solution to generate an aerosol. The air inlet is in communication with the vaporization chamber, and provides air to the heating component when the user inhales. The aerosol generated by the heating component is first generated in the vaporization chamber, and subsequently inhaled by the user via the airflow channel and the air outlet. The power supply device supplies power needed by the heating component, and the control device controls the heating time of the heating component according to an inhalation action of the user detected by the sensing device. The housing wraps all the foregoing components.

Existing electronic cigarette products have different defects, which may result from poor designs of relative positions between different members. For example, common electronic cigarette products are designed to align the heating component, the airflow channel and the air outlet in a vertical direction. Since the airflow has a specific length, the aerosol is cooled when passing through the airflow channel, and a condensed liquid is formed on the airflow channel wall. Under this design, when the condensed liquid reaches a specific volume, the user is likely to inhale the condensed liquid directly and consequently have a bad experience of choking.

In addition, existing electronic cigarette products are not designed to avoid countercurrent flow of condensate. When the electronic cigarette is tilted or placed upside down, the condensed liquid remaining in the vaporization chamber and the airflow channel may leak from the air inlet or the air outlet. The leaking condensed liquid may damage electrical components (for example, the sensing device and the control device) in the electronic cigarette product.

Further, existing electronic cigarette products are not designed to control the power output of the heating component. When the user inhales for a long time, the power supply device continuously heats the heating component, and the heating component may be overheated and produce a burnt smell, causing a bad experience for the user. The overheated heating component may also destroy or burn the internal components of the electronic cigarette. Fast power consumption is also a general disadvantage of existing electronic cigarette products that are not designed to control the output power.

Therefore, a vaporization device and a method thereof are provided to resolve the foregoing problems.

SUMMARY OF THE INVENTION

A vaporization device is provided. The vaporization device includes a cartridge and a body. The cartridge has a housing, a heating component and a heating component base. The housing and the heating component base define an air inlet channel and an air outlet channel, and the heating component and the heating component base define a cavity. The air inlet channel is in communication with the cavity through a first communication portion, and the first communication portion is located between the heating component and the heating component base. The air outlet channel is in communication with the cavity through a second communication portion, and the second communication portion is located between the heating component and the heating component base. The body has an accommodation portion. When the cartridge and the body are removably combined, the accommodation portion covers a portion of the cartridge.

A device configured to store a solution is provided. The device includes a housing, a heating component, a heating component top cap and a heating component base. The housing and the heating component top cap define a storage compartment, and the storage compartment is in communication with the heating component. The housing and the heating component base define an air inlet channel and an air outlet channel, and the heating component and the heating component base define a cavity. The air inlet channel is in communication with the cavity through a first communication portion, the air outlet channel is in communication with the cavity through a second communication portion, and the first communication portion and the second communication portion are located between the heating component and the heating component base.

A method for operating a vaporization device is provided. The method includes causing a first airflow to enter, along an air inlet channel, a cavity between a heating component and a heating component base through a first through hole of a housing, where the air inlet channel is defined by the housing and the heating component base. The method includes causing the first airflow to enter an air outlet channel from the cavity, where the air outlet channel is defined by the housing and the heating component base. The method includes causing the first airflow to leave, through a second through hole on the housing, the cavity along the air outlet channel. The first airflow experiences a first direction change when entering the cavity from the air inlet channel, and experiences a second direction change when entering the air outlet channel from the cavity.

BRIEF DESCRIPTION OF THE DRAWINGS

The aspects of the present invention will become more comprehensible from the following detailed description made with reference to the accompanying drawings. It should be noted that, various features may not be drawn to scale, and the sizes of the various features may be increased or reduced arbitrarily for the purpose of clear description.

The drawings and detailed descriptions use the same reference numerals to indicate same or similar elements. The present invention will be more apparent from the detailed descriptions made with reference to the accompanying drawings.

PREFERRED EMBODIMENT OF THE PRESENT INVENTION

Figure 1A:
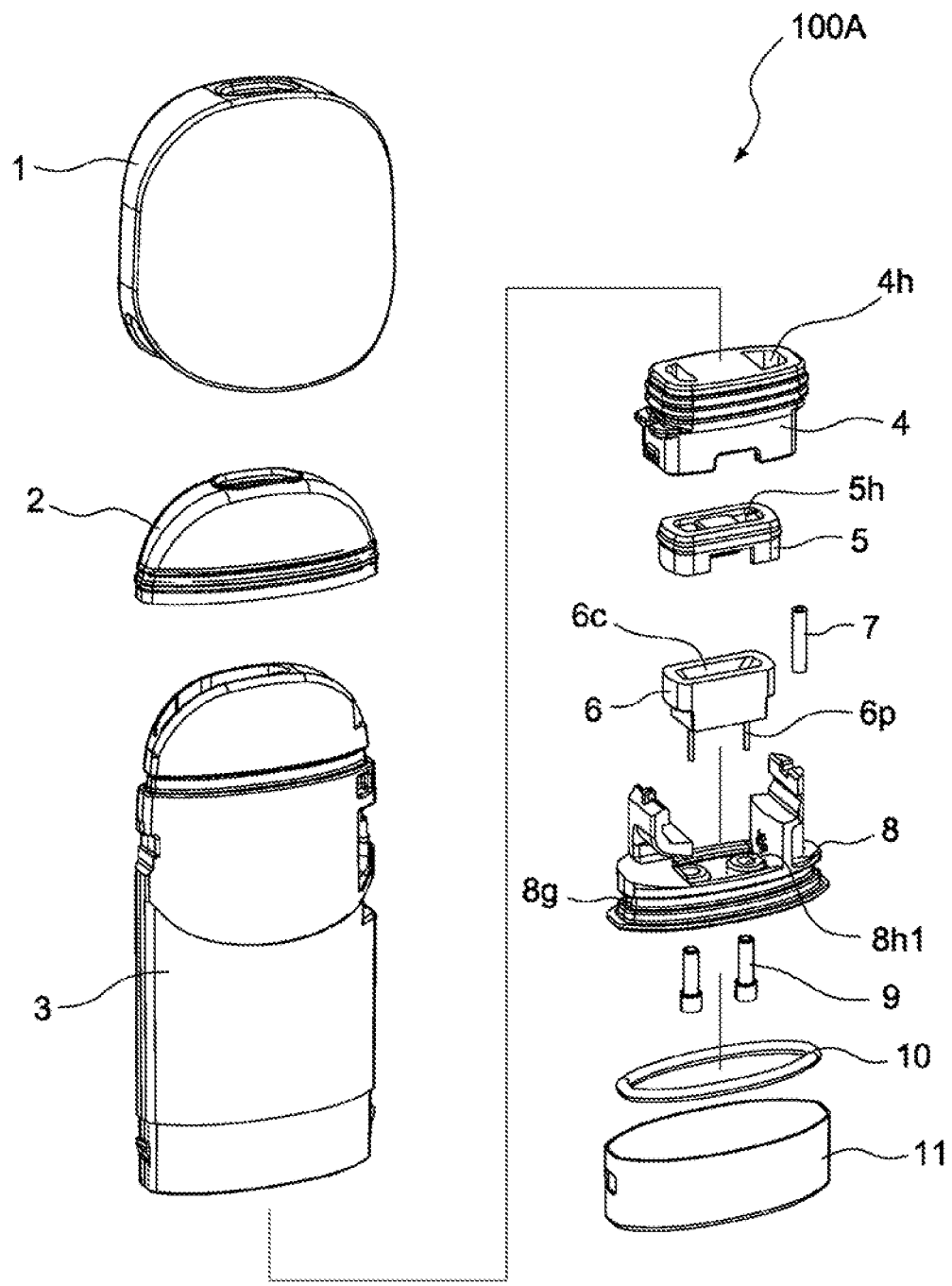
FIG. 1A and FIG. 1B are exploded views of a portion of a vaporization device according to some embodiments of the present invention.

The following disclosed content provides many different embodiments or examples of different features used to implement the provided subject matters. The following describes particular examples of components and deployments. Certainly, there are merely examples and are not intended to be limitative. In the present invention, in the following descriptions, reference formed by the first feature above or on the second feature may include an embodiment formed by direct contact between the first feature and the second feature, and may further include an embodiment in which an additional feature may be formed between the first feature and the second feature to enable the first feature and the second feature to be not in direct contact. In addition, in the present invention, reference numerals and/or letters may be repeated in examples. This repetition is for the purpose of simplification and clarity, and does not indicate a relationship between the described various embodiments and/or configurations.

The embodiments of the present invention are described in detail below. However, it should be understood that, the present invention provides many applicable concepts that can be implemented in various particular cases. The described particular embodiments are only illustrative and do not limit the scope of the present invention.

Figure 1B:
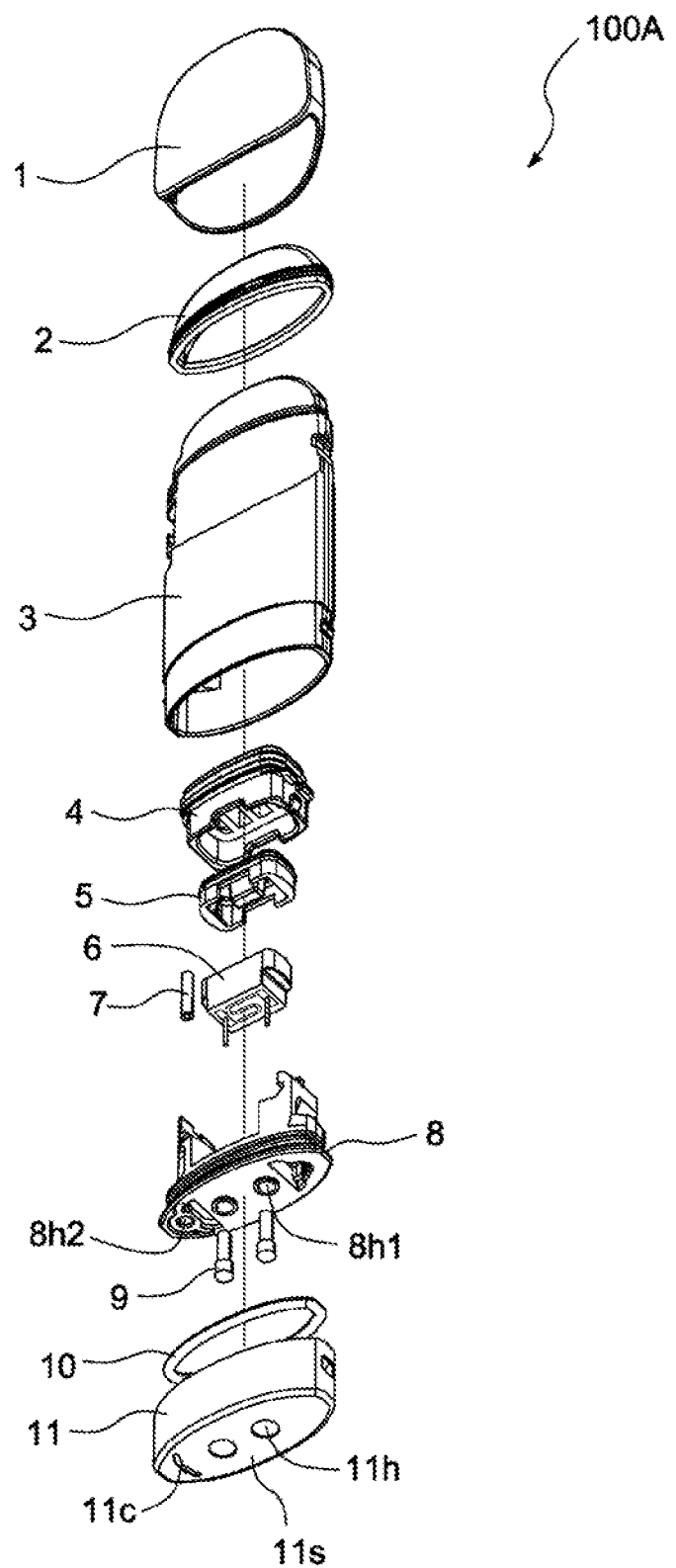

FIG. 1A and FIG. 1B are exploded views of a portion of a vaporization device according to some embodiments of the present invention.

Figure 2A:
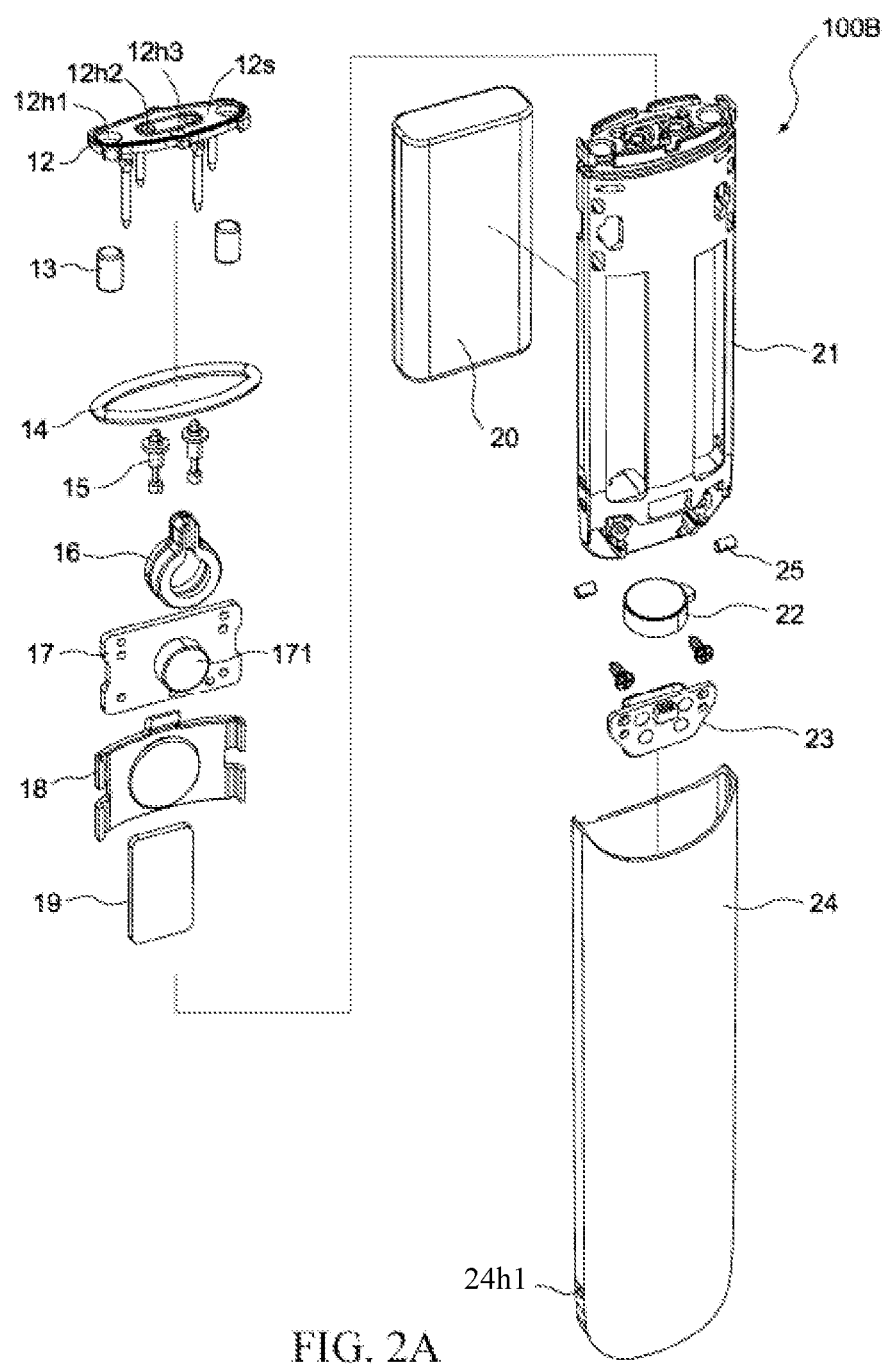
FIG. 2A and FIG. 2B are exploded views of a portion of a vaporization device according to some embodiments of the present invention.
Figure 2B:
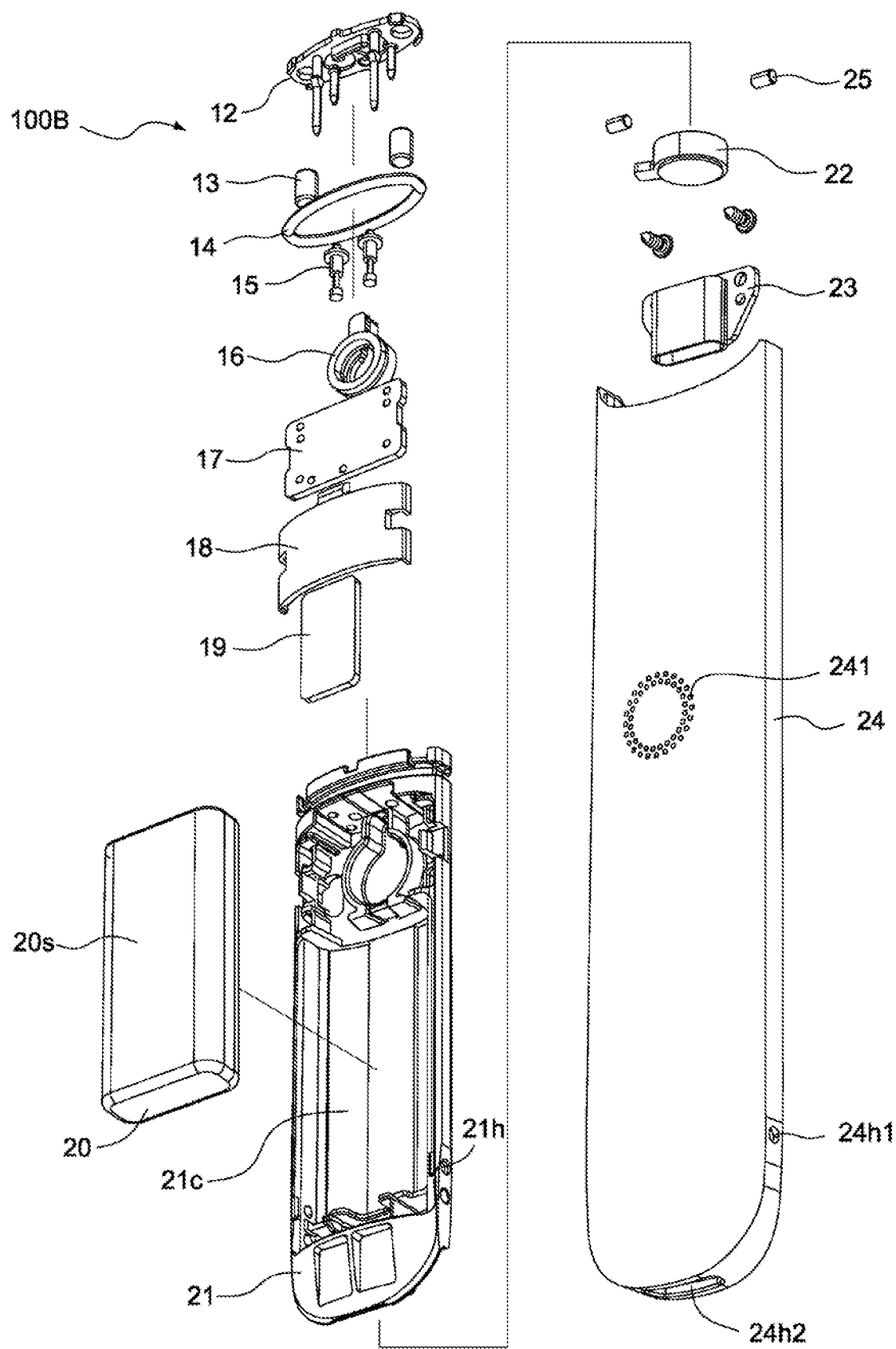

A vaporization device 100 may include a cartridge 100A (shown in FIG. 1A and FIG. 1B) and a body 100B (shown in FIG. 2A and FIG. 2B). In some embodiments, the cartridge 100A and the body 100B may be designed as an integral device. In some embodiments, the cartridge 100A and the body 100B may be designed into two separate components. In some embodiments, the cartridge 100A may be designed to be removably combined with the body 100B. In some embodiments, the cartridge 100A may be designed to be partly received by the body 100B.

The cartridge 100A includes a mouthpiece 1, a silicone mouthpiece seal member 2, a cartridge housing 3, a heating component top cap 4, a silicone heating component seal member 5, a heating component 6, a sensor starter tube 7, a heating component base 8, a conductive contact 9, an base O-ring 10 and a metal cartridge base 11.

The cartridge housing 3 may store a vaporizable material. The cartridge housing 3 may store a vaporizable liquid. The vaporizable material may make contact with the heating component 6 through a through hole 4h on the heating component top cap 4 and a through hole 5h on the silicone heating component seal member 5. The heating component 6 includes a groove 6c, and the vaporizable material may make direct contact with the heating component 6 through an inner wall of the groove 6c. The vaporizable material may be a type of liquid. The vaporizable material may be a type of solution. In subsequent paragraphs of this application, the vaporizable material may be referred to as e-liquid. The e-liquid is edible.

The heating component 6 includes a conductive component 6p. The vaporization device 100 may supply power to the heating component 6 through the conductive component 6p to increase the temperature of the heating component 6.

The sensor starter tube 7 may be a hollow tube. The sensor starter tube 7 may be disposed on a side of the heating component base 8. The sensor starter tube 7 may be disposed on a side of the heating component base 8 close to an air inlet channel. The sensor starter tube 7 may pass through a through hole 8h2 on the heating component base 8. The sensor starter tube 7 may be fixedly disposed on the through hole 8h2 on the heating component base 8. One end of the sensor starter tube 7 may be exposed by a through hole 11c on the metal cartridge base 11.

The conductive contact 9 passes through a through hole 8h1 on the heating component base 8 to make contact with the conductive component 6p of the heating component 6. The conductive contact 9 may make physical contact with the conductive component 6p. The conductive contact 9 may be electrically connected with the conductive component 6p.

The base O-ring 10 may be fixedly disposed in a groove 8g of the heating component base 8. After being combined with each other, the base O-ring 10 and the heating component base 8 are disposed inside the metal cartridge base 11. The metal cartridge base 11 may cover the base O-ring 10. The metal cartridge base 11 may cover at least one part of the heating component base 8.

One end of the conductive contact 9 passes through the through hole 8h1 of the heating component base 8, and the other end of the conductive contact 9 may be exposed by a through hole 11h on the metal cartridge base 11.

FIG. 2A and FIG. 2B are exploded views of a portion of a vaporization device according to some embodiments of the present invention.

The body 100B includes a power component bracket silicone 12, a magnetic component 13, an O-ring 14 of the power component bracket, a conductive probe 15, a sensor 16, a circuit board 17, an light guide component 18, a buffer component 19, a power supply component 20, a power supply component bracket 21, a motor 22, a charging panel 23 and a body housing 24.

The power component bracket silicone 12 may be a component closest to the metal cartridge base 11 in the body 100B. An upper surface 12s of the power component bracket silicone 12 is adjacent to a lower surface 11s of the metal cartridge base 11 as shown in FIG. 1B. The power component bracket silicone 12 includes through holes 12$h$1, 12$h$2, and 12$h$3. One end of the magnetic component 13 may be exposed by the through hole 12$h$1. One end of the conductive probe 15 may be exposed by the through hold 12$h$2.

An attractive force may be generated between the magnetic component 13 and the metal cartridge base 11. The attractive force removably combines the cartridge 100A and the body 100B. In some embodiments, the magnetic component 13 may be a permanent magnet. In some embodiments, the magnetic component 13 may be an electromagnet. In some embodiments, the magnetic component 13 itself has magnetic properties. In some embodiments, the magnetic component 13 has magnetic properties after being energized.

One part of the conductive probe 15 may be exposed by the through hole 12$h$2, and exceeds the upper surface 12$s$ of the power component bracket silicone 12. The conductive probe 15 can be scalable. When the cartridge 100A and the body 100B are removably combined, the conductive probe 15 and the conductive contact 9 make contact with each other. When the cartridge 100A and the body 100B are removably combined, the conductive probe 15 and the conductive contact 9 are electrically connected with each other. When the cartridge 100A and the body 100B are removably combined, the conductive contact 9 compresses the conductive probe 15 and shortens the length of the conductive probe 15. In some embodiments, the conductive probe 15 may be a conductive contact.

The sensor 16 may detect an airflow through the through hole 12$h$3. The sensor 16 may detect a barometric change through the through hole 12$h$3. The sensor 16 may detect a negative pressure through the through hole 12$h$3. The sensor 16 may be used to detect whether an air pressure is lower than a threshold through the through hole 12$h$3. The sensor 16 may detect an acoustic wave through the through hole 12$h$3. The sensor 16 may be used to detect whether an amplitude of the acoustic wave is higher than a threshold through the through hole 12$h$3.

In some embodiments, the sensor 16 may be an airflow sensor. In some embodiments, the sensor 16 may be an air pressure sensor. In some embodiments, the sensor 16 may be an acoustic sensor. In some embodiments, the sensor 16 may be an acoustic receiver. In some embodiments, the sensor 16 may be a microphone.

One side of the circuit board 17 includes a controller 171. The controller 171 may be a microprocessor. The controller 171 may be a programmable integrated circuit. The controller 171 may be a programmable logic circuit. In some embodiments, after the controller 171 is manufactured, arithmetic logic in the controller 171 cannot be changed. In some embodiments, after the controller 171 is manufactured, arithmetic logic in the controller 171 can be changed programmably.

The circuit board 17 may also include a memory (not shown). In some embodiments, the memory may be integrated in the controller 171. In some embodiments, the memory and the controller 171 may be separately disposed.

The controller 171 may be electrically connected to the sensor 16. The controller 171 may be electrically connected to the conductive probe 15. The controller 171 may be electrically connected to the power supply component 20. When the sensor 16 detects an airflow, the controller 171 may control the power supply component 20 to supply power to the conductive probe 15. When the sensor 16 detects a barometric change, the controller 171 may control the power supply component 20 to supply power to the conductive probe 15. When the sensor 16 detects a negative pressure, the controller 171 may control the power supply component 20 to supply power to the conductive probe 15. When the controller 171 determines that an air pressure that the sensor 16 detects is lower than a threshold, the controller 171 may control the power supply component 20 to supply power to the conductive probe 15. When the sensor 16 detects an acoustic wave, the controller 171 may control the power supply component 20 to supply power to the conductive probe 15. When the controller 171 determines that an amplitude of the acoustic wave that the sensor 16 detects is higher than a threshold, the controller 171 may control the power supply component 20 to supply power to the conductive probe 15.

The other side of the circuit board 17 may include one or more luminous components (not shown). According to different operation states of the vaporization device 100, the controller 171 may control the one or more luminous components on the circuit board 17 to produce different visual effects. In some embodiments, the one or more luminous components on the circuit board 17 may be arranged into an array. In some embodiments, the array of the one or more luminous components may have one or more rows. In some embodiments, the array of the one or more luminous components may have one or more columns.

In some embodiments, when a user inhales from the vaporization device 100, the controller 171 may control the one or more luminous components to produce a visual affect. In some embodiments, when the user charges the vaporization device 100, the controller 171 may control the one or more luminous components to produce a visual affect. In some embodiments, based on a quantity of electricity of the power supply component 20, the controller 171 may control the one or more luminous components to produce a visual affect. In some embodiments, the visual effect produced by the one or more luminous components may include blinking, intermittent illumination or continuous illumination. In some embodiments, the controller 171 may control the brightness produced by the one or more luminous components. In some embodiments, the controller 171 may control the array of the one or more luminous components to display a specific pattern. In some embodiments, the controller 171 may control two luminous components that have different colors to illuminate and generate a mixed chromatic light.

The light guide component 18 is disposed on a side that is of the circuit board 17 and that includes one or more luminous components. A light generated by the one or more luminous components can be refracted after passing through the light guide component 18. A light generated by the one or more luminous components can be scattered after passing through the light guide component 18. The light guide component 18 may make the light emitted from the one or more luminous components on the circuit board 17 more uniform.

The power supply component 20 may be disposed in a groove 21$c$ of the power supply component bracket 21. The buffer component 19 may be disposed on a surface 20$s$ of the power supply component 20. The buffer component 19 may be disposed between the power supply component 20 and the body housing 24. The buffer component 19 may make direct contact with the surface 20$s$ of the power supply component 20 and an inner wall of the body housing 24. An extra buffer component may be disposed between the power supply component 20 and the groove 21, even though it is not shown in the drawings.

In some embodiments, the power supply component 20 may be a battery. In some embodiments, the power supply component 20 may be a rechargeable battery. In some embodiments, the power supply component 20 may be a disposable battery.

The power supply component bracket 21 may be fixedly connected with the body housing 24 by a fixing component 25. The fixing component 25 may fixedly connect the power supply component bracket 21 and the body housing 24 through a through hole 21$h$ on the power supply component bracket 21 and a through hole 24$h1$ on the body housing 24.

The motor 22 may be electrically connected to the controller 171. Based on different operation states of the vaporization device 100, the controller 171 may control the motor 22 to produce different somatosensory effects. In some embodiments, when the user inhales for more than a specific length of time, the controller 171 may control the motor 22 to vibrate, so as to remind the user to stop inhaling. In some embodiments, when the user charges the vaporization device 100, the controller 171 may control the motor 22 to vibrate, so as to indicate that charging has started. In some embodiments, when the vaporization device 100 has been charged, the controller 171 may control the motor 22 to vibrate, so as to indicate that charging has been completed.

The charging panel 23 is disposed on the bottom of the body housing 24. One end of the charging panel 23 is exposed by a through hole 24$h2$ of the body housing 24. The power supply component 20 can be charged by the charging panel 23.

The body housing 24 includes a light transmitting component 241. The light transmitting component 241 may include one or more holes penetrating the body housing 24. In some embodiments, the light transmitting component 241 may appear in a generally circular shape. In some embodiments, the light transmitting component 241 may appear in a generally rectangle shape. In some embodiments, the light transmitting component 241 may appear in a generally symmetrical shape. In some embodiments, the light transmitting component 241 may appear in a generally asymmetrical shape. Light emitted by the one or more luminous components on the circuit board 17 is visible via the light transmitting component 241.

Figure 3A:
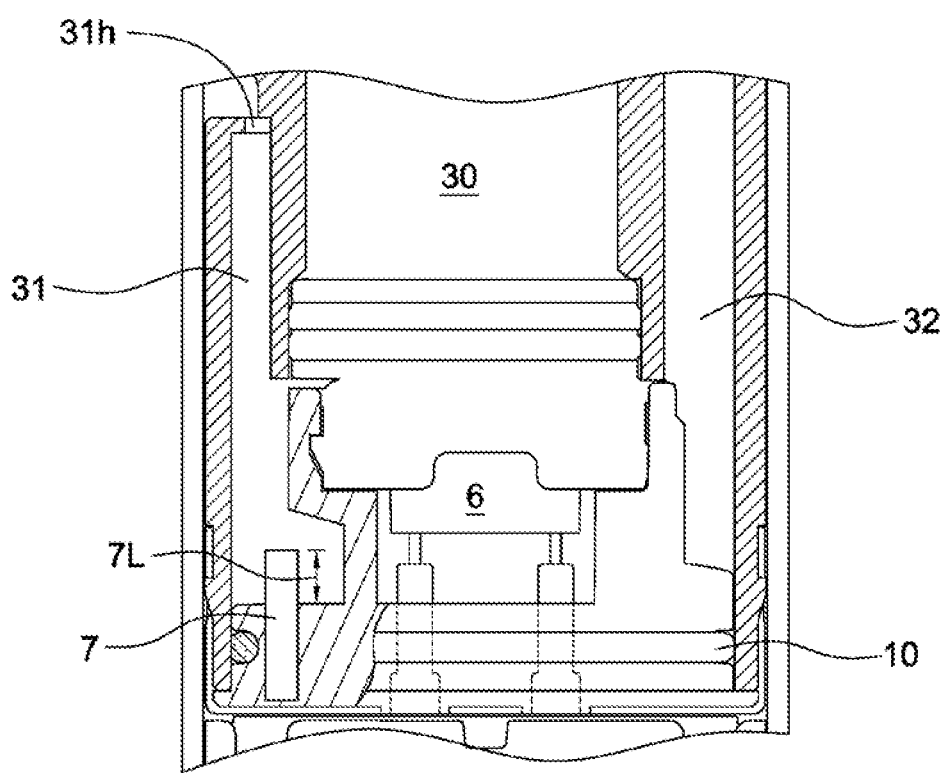
FIG. 3A and FIG. 3B are sectional views of a cartridge according to some embodiments of the present invention.
Figure 3B:
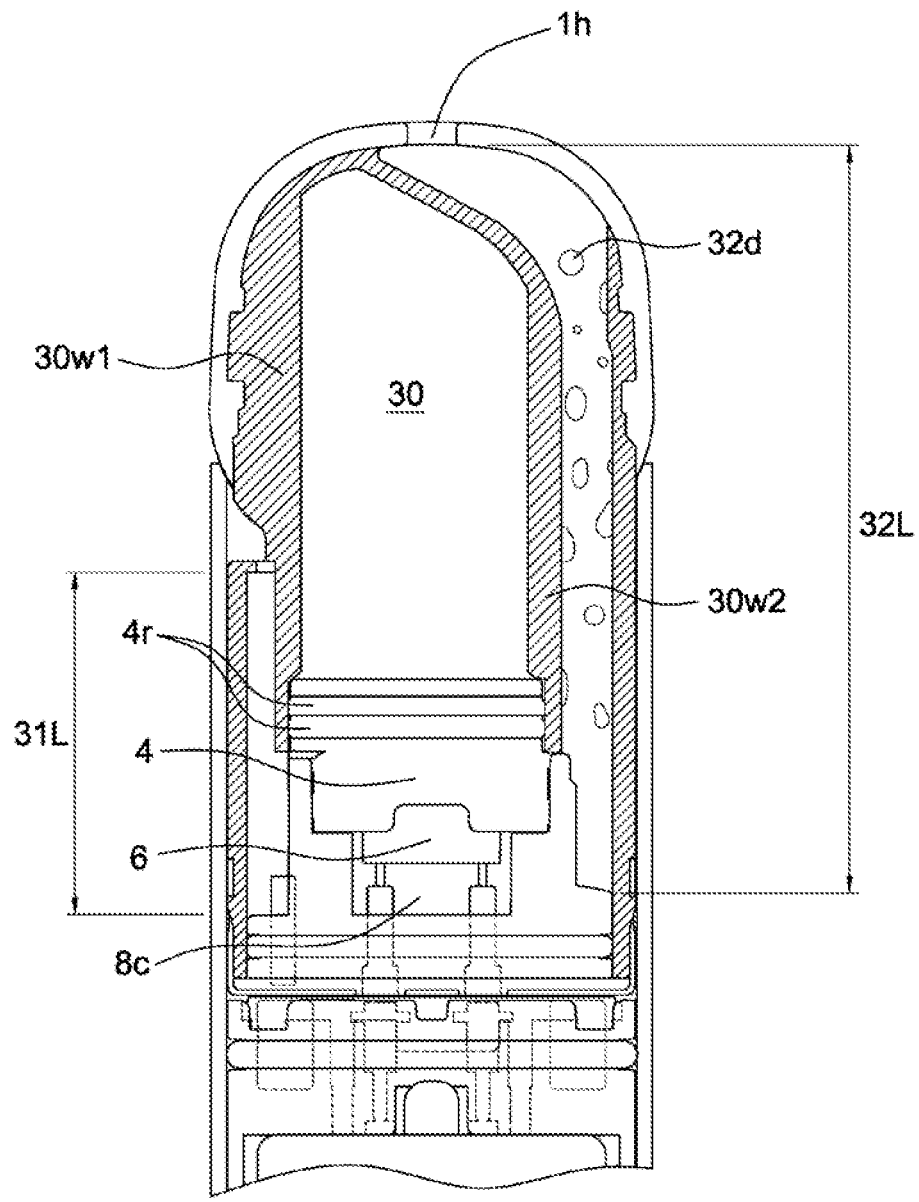

FIG. 3A and FIG. 3B are sectional views of a cartridge according to some embodiments of the present invention.

As shown in FIG. 3A, the cartridge housing 3 includes an e-liquid storage compartment 30, an air inlet channel 31 and an air outlet channel 32. In some embodiments, the air inlet channel 31 and the air outlet channel 32 may be located inside the cartridge housing 3. In some embodiments, the air inlet channel 31 and the air outlet channel 32 may be defined by an internal structure of the cartridge housing 3. In some embodiments, the air inlet channel 31 and the air outlet channel 32 may be defined by the cartridge housing 3 and the body housing 24 together. In some embodiments, the air inlet channel 31 may be defined by the internal structure of the housing 3 and the heating component base 8 together. In some embodiments, the air outlet channel 32 may be defined by the internal structure of the housing 3 and the heating component base 8 together.

The air inlet channel 31 is located on one side of the cartridge housing 3, and the air outlet channel 32 is located on the other side of the cartridge housing 3. In some embodiments, the air inlet channel 31 may be located on one side of the heating component 6, and the air outlet channel 32 may be located on the other side of the heating component 6 opposite to the air inlet channel 31.

In some embodiments, the pipe diameter of the air inlet channel 31 may be the same as that of the air outlet channel 32. In some embodiments, the pipe diameter of the air inlet channel 31 may be different from that of the air outlet channel 32. In some embodiments, the pipe diameter of the air inlet channel 31 may be smaller than that of the air outlet channel 32. Smaller pipe diameter of the air inlet channel 31 may make it easier for the sensor starter tube 7 to generate a negative pressure. Smaller pipe diameter of the air inlet channel 31 may make it easier for the sensor 16 to detect an inhalation action of the user.

In some embodiments, the air inlet channel 31 and the air outlet channel 32 may be configured asymmetrically in the cartridge housing 3.

As shown in FIG. 3A, the vaporization chamber 8$c$ may be a cavity between the heating component 6 and the heating component base 8. As shown in FIG. 3A, the vaporization chamber 8$c$ may be defined by the heating component 6 and the heating component base 8 together. The air inlet channel 31 is in communication with the vaporization chamber 8$c$. The air outlet channel 32 is in communication with the vaporization chamber 8$c$. The part where the air inlet channel 31 is in communication with the vaporization chamber 8$c$ is located below the heating component 6. The part where the air outlet channel 32 is in communication with the vaporization chamber 8$c$ is located below the heating component 6. The foregoing configuration has many advantages. The configuration can at least partially vent the airflow away from the heating component 6. The configuration can at least partially prevent the airflow from flowing directly through the heating component 6. Compared to the prior art where the airflow needs to pass directly through the heating component, the effect of a material of the heating component on the flavor of e-liquid (vaporizable material) is reduced. In addition, when the user vertically holds the vaporization device 100, the condensed liquid remaining on the inner wall of the air inlet channel dose not drip on the heating component 6 even if it flows backwards, so that the condensed liquid can be prevented from clogging the heating component 6.

As shown in FIG. 3A, the sensor starter tube 7 is disposed on the heating component base 8. The length of the sensor starter tube 7 that protrudes from the heating component base 8 is 7L. The part of the sensor starter tube 7 protruding from the heating component base 8 can be disposed in the air inlet channel 31. When the vaporization device 100 is being used, an aerosol may condense into a liquid 32$d$ and remain on an inner wall of the air outlet channel 32. The liquid 32$d$ may flow back and accumulate in an e-liquid tank 8$t$ (refer to FIG. 8A to FIG. 8D). In some circumstances, the vaporizable material stored in the e-liquid storage compartment 30 may also leak into the e-liquid tank 8$t$ through the bottom of the heating component 6. The part of the sensor starter tube 7 exceeding the heating component base 8 can present the liquid stored in the e-liquid tank 8$t$ from leaking through the through hole 8$h2$.

In some embodiments, the length 7L is within a range of 1 mm to 10 mm. In some embodiments, the length 7L is within a range of 1 mm to 6 mm. In some embodiments, the length 7L is within a range of 1 mm to 4 mm. In some embodiments, the length 7L is within a range of 1 mm to 2 mm. In some embodiments, the length 7L may be 1.5 mm. In some embodiments, the length 7L may be 2 mm.

In some embodiments, the sensor starter tube 7 and the heating component base 8 may be two separate components. In some embodiments, the sensor starter tube 7 and the heating component base 8 may be formed integrally. In some embodiments, the sensor starter tube 7 may be made of a metal material. In some embodiments, the sensor starter tube 7 may be made of a plastic material. In some embodiments, the sensor starter tube 7 and the heating component base 8 may be made of a same material. In some embodiments, the sensor starter tube 7 and the heating component base 8 may be made of different materials.

As shown in FIG. 3B, the length of the air inlet channel 31 is 31L, and the length of the air outlet channel 32 is 32L. In some embodiments, the length 31L may be different from the length 32L. In some embodiments, the length 31L may be less than the length 32L.

The length 7L and the length 31L may be in a proportional relationship. In some embodiments, a proportion of the length 31L and the length 7L may be within a range of 6 to 7. In some embodiments, a proportion of the length 31L and the length 7L may be within a range of 7 to 8. In some embodiments, a proportion of the length 31L and the length 7L may be within a range of 8 to 9. In some embodiments, a proportion of the length 31L and the length 7L may be within a range of 9 to 10.

The air inlet channel 31 is in communication with the external through a through hole 31h on the cartridge housing 3. The air outlet channel 32 is in communication with the outside through a through hole 1h on the mouthpiece 1. In some embodiments, the through hole 31h and the through hole 1h are located in different positions in the horizontal direction. In some embodiments, the distance between the through hole 31h and the heating component 6 is different from the distance between the through hole 1h and the heating component 6. In some embodiments, the distance between the through hole 31h and the heating component 6 is less than the distance between the through hole 1h and the heating component 6.

The e-liquid storage compartment 30 is a sealed area. The e-liquid storage compartment 30 may be formed by compartment structures 30w1 and 30w2 in the cartridge housing 3 and the heating component top cap 4. A part where the heating component top cap 4 makes contact with the compartment structures 30w1 and 30w2 has a sealing member 4r. The sealing member 4r makes the heating component top cap 4 and the compartment structures 30w1 and 30w2 closely in contact with each other. The sealing member 4r may prevent the vaporizable material stored in the e-liquid storage compartment 30 from leaking out.

In some embodiments, the heating component top cap 4 and the sealing member 4r may be formed by using a same process. In some embodiments, the heating component top cap 4 and the sealing member 4r may be formed by using a same process and different materials. In some embodiments, the heating component top cap 4 and the sealing member 4r may be formed by injection molding. In some embodiments, the heating component top cap 4 may be produced by injection molding using a plastic material. In some embodiments, the sealing member 4r may be produced by injection molding using liquid silica on the heating component top cap 4.

In some embodiments, the heating component top cap 4 and the sealing member 4r may be formed by using different processes and subsequently combined with each other. In some embodiments, the heating component top cap 4 is produced by injection molding using a plastic material, and the sealing member 4r is produced by compression molding. The heating component top cap 4 and the sealing member 4r are combined with each other by using an additional component step.

Figure 4:
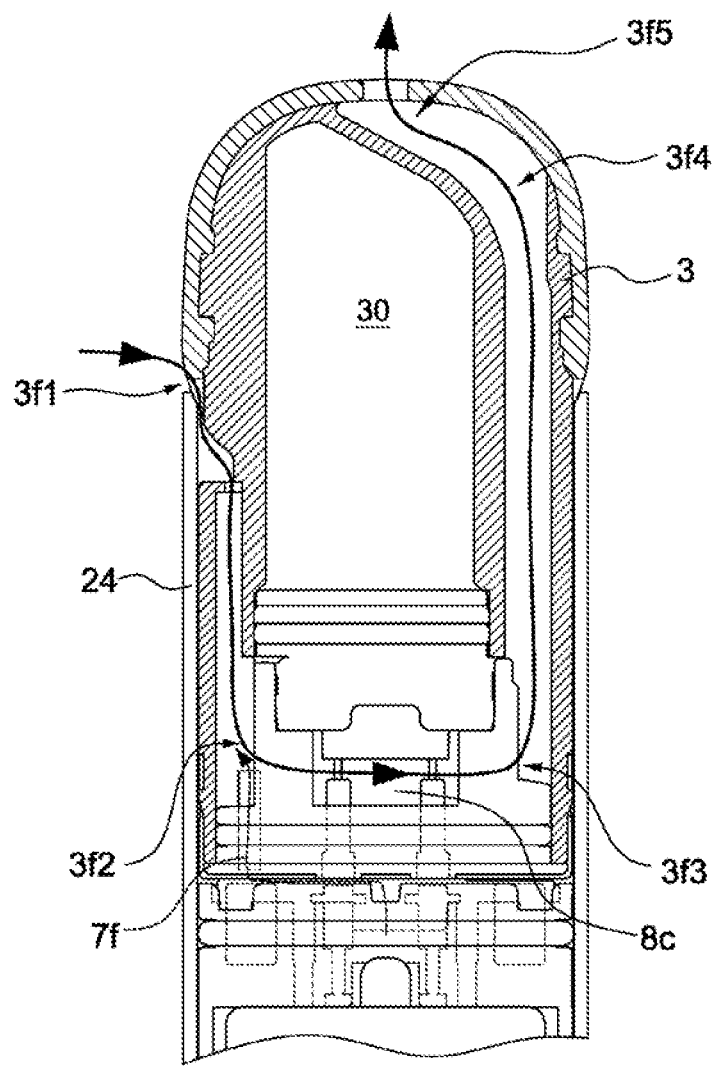
FIG. 4 is a sectional view of a cartridge according to some embodiments of the present invention.

FIG. 4 is a sectional view of a cartridge according to some embodiments of the present invention.

FIG. 4 shows a gas channel structure in the cartridge 100A.

The air inlet channel 31 extends in a direction (the vertical direction shown in FIG. 4). The communication portion 31c (refer to FIG. 8D) of the air inlet channel 31 and the vaporization chamber 8c extends in a direction (the horizontal direction in FIG. 4). The direction in which the air inlet channel 31 extends is different from the direction in which the communication portion 31c extends.

The air outlet channel 32 extends in a direction (the vertical direction shown in the drawings). The communication portion 32c (refer to FIG. 8D) of the air outlet channel 32 and the vaporization chamber 8c extends in a direction (the horizontal direction in the drawings). The direction in which the air outlet channel 32 extends is different from the direction in which the communication portion 32c extends.

The air outlet channel 32 may have a first portion (shown in FIG. 4, the part between 3f3 and 3f4) and a second portion (shown in FIG. 4, the part between 3f4 and 3f5). The direction in which the first portion extends may be different from the direction in which the second portion extends.

The part where the air inlet channel 31 is in communication with the vaporization chamber 8c has a direction change 3f2. The part where the air outlet channel 32 is in communication with the vaporization chamber 8c has a direction change 3f3. The part of the air outlet channel 32 close to the through hole 1h of the mouthpiece 1 has a direction change 3f4. The part of the air outlet channel 32 in communication with the through hole 1h of the mouthpiece 1 has a direction change 3f5.

FIG. 4 shows an airflow direction generated when the user inhales from the cartridge 100A. When the user inhales, air enters from a gap between the cartridge 100A and the body housing 24, and experiences the direction change 3f1 between the cartridge 100A and the body housing 24. Subsequently, the air enters the air inlet channel 31 through the through hole 31h, and experiences the direction change 3f2 before entering the vaporization chamber 8c.

An airflow 7f is generated in the sensor starter tube 7 by the inhalation action of the user. The airflow 7f enters the cartridge 100A from the sensor starter tube 7. In some embodiments, the airflow 7f may enter the air inlet channel 31. In some embodiments, the airflow 7f may enter the vaporization chamber 8c with the inhalation action of the user. In some embodiments, part of the airflow 7f may enter the air outlet channel 32 with the inhalation action of the user.

The airflow 7f is detected by the sensor 16 when passing through a gap between the cartridge 100A and the body 100B. The controller 171 activates the heating component 6 based on a detection result of the sensor 16, and generates an aerosol in the vaporization chamber 8c. The generated aerosol experiences the direction change 3f3 when the aerosol just enters the air outlet channel 32. The generated aerosol subsequently experiences the another direction change 3f4 at the through hole 1h in the air outlet channel 32 close to the mouthpiece 1. The generated aerosol experiences the another direction change 3f5 when leaving the through hole 1h on the mouthpiece 1.

When the vaporization device 100 is being used, the aerosol may condense into a liquid 32d and remain on an inner wall of the air outlet channel 32. The condensed liquid 32d is viscous and does not easily flow on the inner wall of the air outlet channel 32. When the user is inhaling, the plurality of direction changes 3f3, 3f4 and 3f5 included in the air outlet channel 32 may preferably prevent the condensed liquid 32d from being inhaled by the user through the through hole 1h.

The airflow has a temperature rise Tr after passing through the vaporization chamber 8c from the air inlet channel 31. In some embodiments, the temperature rise Tr may be within a range of 200° C. to 220° C. In some embodiments, the temperature rise Tr may be within a range of 240° C. to 260° C. In some embodiments, the temperature rise Tr may be within a range of 260° C. to 280° C. In some embodiments, the temperature rise Tr may be within a range of 280° C. to 300° C. In some embodiments, the temperature rise Tr may be within a range of 300° C. to 320° C. In some embodiments, the temperature rise Tr may be within a range of 200° C. to 320° C.

An airflow from the vaporization chamber 8c may has a temperature drop Tf before reaching the through hole 1h. The airflow from the vaporization chamber 8c may has a temperature drop Tf when passing through the air outlet channel 32. In some embodiments, the temperature drop Tf may be within a range of 145° C. to 165° C. In some embodiments, the temperature drop Tf may be within a range of 165° C. to 185° C. In some embodiments, the temperature drop Tf may be within a range of 205° C. to 225° C. In some embodiments, the temperature drop Tf may be within a range of 225° C. to 245° C. In some embodiments, the temperature drop Tf may be within a range of 245° C. to 265° C. In some embodiments, the temperature drop Tf may be within a range of 145° C. to 265° C.

In some embodiments, the aerosol inhaled by the user via the through hole 1h can have a temperature below 65° C. In some embodiments, the aerosol inhaled by the user via the through hole 1h can have a temperature below 55° C. In some embodiments, the aerosol inhaled by the user via the through hole 1h can have a temperature below 50° C. In some embodiments, the aerosol inhaled by the user via the through hole 1h can have a temperature below 45° C. In some embodiments, the aerosol inhaled by the user via the through hole 1h can have a temperature below 40° C.

Figure 5A:
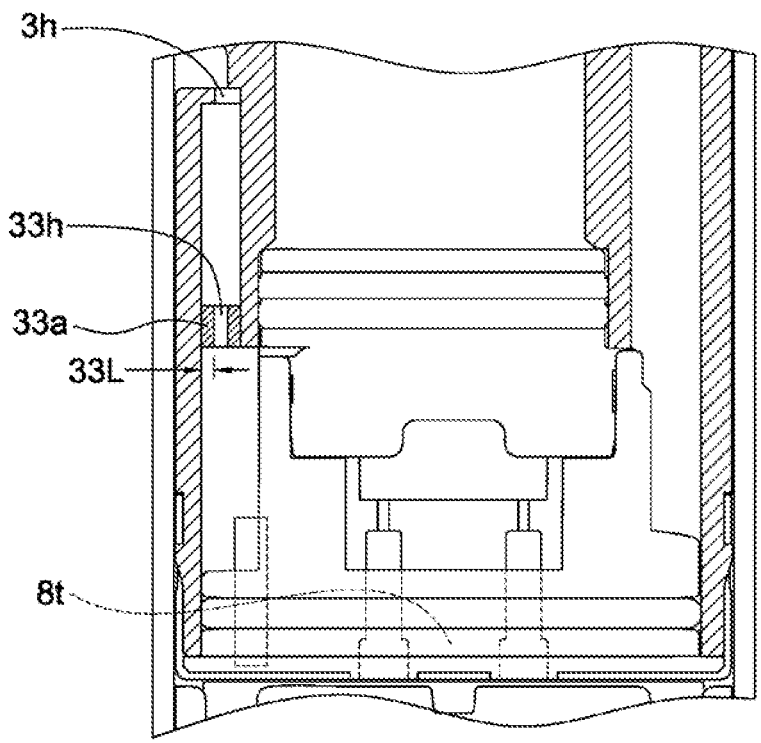
FIG. 5A and FIG. 5B are sectional views of a cartridge according to some embodiments of the present invention.
Figure 5B:
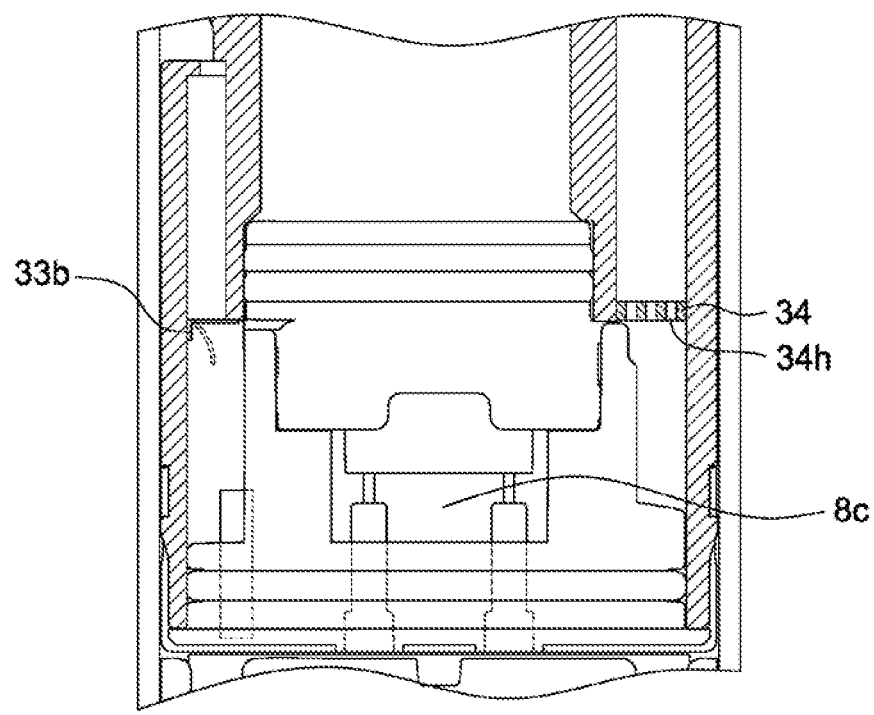

FIG. 5A and FIG. 5B are sectional views of a cartridge according to some embodiments of the present invention.

As shown in FIG. 5A, a blocking component 33a may be disposed in the air inlet channel 31. The blocking component 33a may have a through hole 33h. A diameter of the through hole 33h is smaller than the pipe diameter of the air inlet channel 31. The through hole 33h may be regarded as a portion of the air inlet channel 31. The thickness of the blocking component 33a is 33L. The thickness 33L of the block component 33a results in a height drop in the air inlet channel 31. Since the liquid or the e-liquid stored in the e-liquid tank 8t is viscous, the height drop facilitates preventing the liquid or the e-liquid stored in the e-liquid tank 8t from flowing backwards. The height drop facilitates preventing the liquid or the e-liquid stored in the e-liquid tank 8t from leaking via the through hole 31h.

In some embodiments, the block component 33a may be made of silica gel. In some embodiments, the block component 33a may be a silicone ring. In some embodiments, the block component 33a and the housing 3 may be made of a same material. In some embodiments, the block component 33a and the housing 3 may be made of different materials. In some embodiments, the block component 33a and the housing 3 may be two separate components. In some embodiments, the block components 33a and the housing 3 may be formed integrally.

As shown in FIG. 5B, a blocking component 33b may be disposed in the air inlet channel 31. The blocking component 33b may cause the air to enter the air inlet channel 31 through the through hole 31h. The block component 33b may prevent the liquid from flowing from the e-liquid tank 8t to the through hole 31h. In some embodiments, the block component 33b may be a check valve.

A blocking component 34 may be disposed in the air outlet channel 32. The blocking component 34 may have one or more through holes 34h. The blocking component 34 may cause the aerosol to flow from the vaporization chamber 8c to the through hole 1h. Since the liquid or e-liquid stored in the e-liquid tank 8t is viscous, the hole diameter of the through hole 34h is designed to prevent the liquid or the e-liquid from flowing from the e-liquid tank 8t to the through hole 1h.

FIG. 6A, FIG. 6B, FIG. 6C, FIG. 6D and FIG. 6E are top views of a heating component top cap according to some embodiments of the present invention.

The e-liquid stored in the e-liquid storage compartment 30 may make contact with the heating component 6 through a through hole 4h on the heating component top cap 401 and a through hole 5h on the silicone heating component seal member 5.

The hold diameter and shape of the through hole 4h may be adjusted according to the property of the e-liquid. In some embodiments, if the viscosity of the e-liquid is relatively high, the hole diameter of the through hole 4h can be designed relatively big. In some embodiments, if the viscosity of the e-liquid is relatively low, the hole diameter of the through hole 4h can be designed relatively small. The through hole 4h with a relatively small hole diameter may prevent excessive e-liquid from making direct contact with the heating component 6. The through hole 4h with a relatively big hole diameter may ensure more e-liquid to make direct contact with the heating component 6.

The hole diameter of the through hole 4h may be appropriately adjusted according to the property of the e-liquid, so that the heating component 6 can make contact with enough e-liquid to avoid dry burning during heating and prevent the generated aerosol from having a burnt odor.

The hole diameter of the through hole 4h may be appropriately adjusted according to the property of the e-liquid to prevent the heating component 6 from making contact with excessive e-liquid. The excessive e-liquid cannot be adsorbed by the heating component 6, and gradually permeates from the e-liquid storage compartment 30 to the e-liquid tank 8t through the heating component 6. If the amount of e-liquid permeating into the e-liquid tank 8t is excessively large, the probability of the e-liquid flowing into the air inlet channel 31 and the air outlet channel 32 will increase. If the amount of e-liquid permeating into the e-liquid tank 8t is excessively large, the probability of the e-liquid permeating out of the through hole 31h of the air inlet channel and the through hole 32h of the air outlet channel will increase.

Figure 6A:
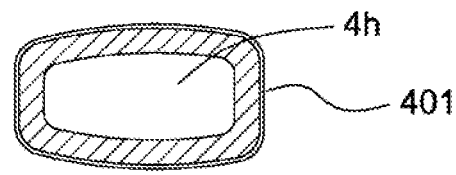
FIG. 6A, FIG. 6B, FIG. 6C, FIG. 6D and FIG. 6E are top views of heating component top caps according to some embodiments of the present invention.

As shown in FIG. 6A, a single through hole 4h may be disposed on the heating component top cap 401. A shape of the through hole 4h is substantially the same as that of the heating component top cap 401. In some embodiments, the aperture area of the through hole 4h is approximately 80% to 90% of the sectional area of the heating component top cap 401. In some embodiments, the aperture area of the through hole 4h is approximately 70% to 80% of the sectional area of the heating component top cap 401.

A through hole 5h may be disposed on the silicone heating component seal member 5 used to match with the heating component top cap 401. The through hole 5h may have a similar shape with that of the through hole 4h on the heating component top cap 401. The through hole 5h may have a similar aperture area with that of the through hole 4h on the heating component top cap 401. The through hole 5h may have a similar position with that of the through hole 4h on the heating component top cap 401. In some embodiments, the through hole 5h may have a different shape from that of the through hole 4h on the heating component top cap 401. In some embodiments, the through hole 5h may have a different position from that of the through hole 4h on the heating component top cap 401. In some embodiments, the through hole 5h may have a different aperture area from that of the through hole 4h on the heating component top cap 401.

Figure 6B:
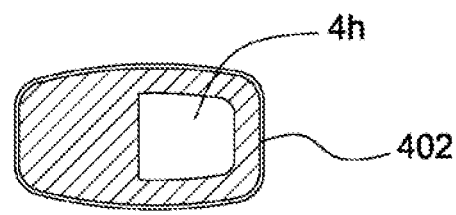

As shown in FIG. 6B, a single through hole 4h may be disposed on the heating component top cap 402. A shape of the through hole 4h is different from that of the heating component top cap 401. In some embodiments, the aperture area of the through hole 4h is approximately 50% to 60% of the sectional area of the heating component top cap 401. In some embodiments, the aperture area of the through hole 4h is approximately 40% to 50% of the sectional area of the heating component top cap 401. In some embodiments, the aperture area of the through hole 4h is approximately 30% to 40% of the sectional area of the heating component top cap 401.

A through hole 5h may be disposed on the silicone heating component seal member 5 used to match with the heating component top cap 402. The through hole 5h may have a similar shape with that of the through hole 4h on the heating component top cap 402. The through hole 5h may have a similar aperture area with that of the through hole 4h on the heating component top cap 402. The through hole 5h may have a similar position with that of the through hole 4h on the heating component top cap 402. In some embodiments, the through hole 5h may have a different shape from that of the through hole 4h on the heating component top cap 402. In some embodiments, the through hole 5h may have a different position from that of the through hole 4h on the heating component top cap 402. In some embodiments, the through hole 5h may have a different aperture area from that of the through hole 4h on the heating component top cap 402.

Figure 6C:
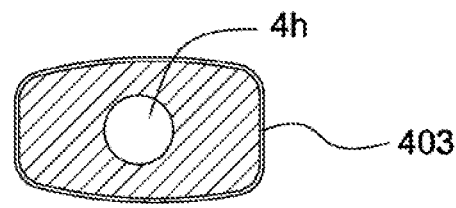

As shown in FIG. 6C, a single through hole 4h may be disposed on the heating component top cap 403. The through hole 4h is substantially in a circular shape. In some embodiments, the aperture area of the through hole 4h is approximately 3 mm$^2$ to 4 mm$^2$ In some embodiments, the aperture area of the through hole 4h is approximately 4 mm$^2$ to 5 mm$^2$ In some embodiments, the aperture area of the through hole 4h is approximately 5 mm$^2$ to 6 mm$^2$ In some embodiments, the aperture area of the through hole 4h is approximately 6 mm$^2$ to 7 mm$^2$ In some embodiments, the aperture area of the through hole 4h is approximately 7 mm$^2$ to 8 mm$^2$ In some embodiments, the aperture area of the through hole 4h is approximately 5.5 mm$^2$.

A through hole 5h may be disposed on the silicone heating component seal member 5 used to match with the heating component top cap 403. The through hole 5h may have a similar shape with that of the through hole 4h on the heating component top cap 403. The through hole 5h may have a similar aperture area with that of the through hole 4h on the heating component top cap 403. The through hole 5h may have a similar position with that of the through hole 4h on the heating component top cap 403. In some embodiments, the through hole 5h may have a different shape from that of the through hole 4h on the heating component top cap 403. In some embodiments, the through hole 5h may have a different position from that of the through hole 4h on the heating component top cap 403. In some embodiments, the through hole 5h may have a different aperture area from that of the through hole 4h on the heating component top cap 403.

Figure 6D:
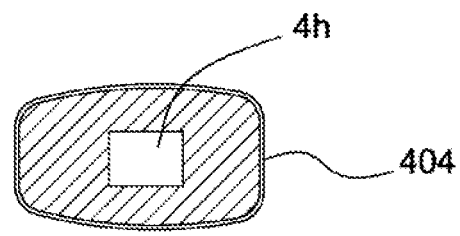

As shown in FIG. 6D, a single through hole 4h may be disposed on the heating component top cap 404. The through hole 4h is substantially in a rectangle shape. In some embodiments, the aperture area of the through hole 4h is approximately 3 mm$^2$ to 4 mm$^2$ In some embodiments, the aperture area of the through hole 4h is approximately 4 mm$^2$ to 5 mm$^2$ In some embodiments, the aperture area of the through hole 4h is approximately 5 mm$^2$ to 6 mm$^2$ In some embodiments, the aperture area of the through hole 4h is approximately 6 mm$^2$ to 7 mm$^2$ In some embodiments, the aperture area of the through hole 4h is approximately 7 mm$^2$ to 8 mm$^2$ In some embodiments, the aperture area of the through hole 4h is approximately 5.5 mm$^2$.

A through hole 5h may be disposed on the silicone heating component seal member 5 used to match with the heating component top cap 404. The through hole 5h may have a similar shape with that of the through hole 4h on the heating component top cap 404. The through hole 5h may have a similar aperture area with that of the through hole 4h on the heating component top cap 404. The through hole 5h may have a similar position with that of the through hole 4h on the heating component top cap 404. In some embodiments, the through hole 5h may have a different shape from that of the through hole 4h on the heating component top cap 404. In some embodiments, the through hole 5h may have a different position from that of the through hole 4h on the heating component top cap 404. In some embodiments, the through hole 5h may have a different aperture area from that of the through hole 4h on the heating component top cap 404.

Although not illustrated in the drawings, it is considered that the through hole 4h has a shape other than a circle and a rectangle.

Figure 6E:
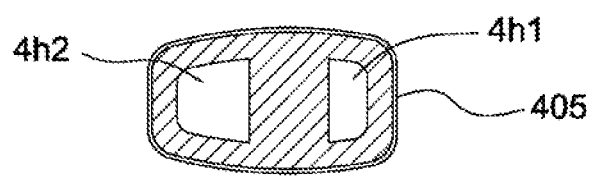

As shown in FIG. 6E, through holes 4h1 and 4h2 may be disposed on the heating component top cap 405. The through hole 4h1 may be disposed on one side of the heating component top cap 405. The through hole 4h2 may be disposed on the other side of the heating component top cap 405. In some embodiments, the aperture area of the through hole 4h1 and the aperture area of the through hole 4h2 may be the same. In some embodiments, the aperture area of the through hole 4h1 and the aperture area of the through hole 4h2 may be different. In some embodiments, the aperture area of the through hole 4h1 may be smaller than the aperture area of the through hole 4h2.

Two through holes may be disposed on the silicone heating component seal member 5 used to match with the heating component top cap 405. The two through holes on the silicone heating component seal member 5 and the through holes 4h1 and 4h2 on the heating component top cap 404 may have similar shapes. The two through holes on the silicone heating component seal member 5 and the through holes 4h1 and 4h2 on the heating component top cap 404 may have similar aperture areas. The two through holes on the silicone heating component seal member 5 and the through holes 4h1 and 4h2 on the heating component top cap 404 may have similar positions. In some embodiments, the two through holes on the silicone heating component seal member 5 and the through holes 4h1 and 4h2 on the heating component top cap 404 may have different shapes. The two through holes on the silicone heating component seal member 5 and the through holes 4h1 and 4h2 on the heating component top cap 404 may have different positions. The two through holes on the silicone heating component seal member 5 and the through holes 4h1 and 4h2 on the heating component top cap 404 may have different aperture areas.

FIG. 7A, FIG. 7B, FIG. 7C and FIG. 7D are schematic diagrams of a heating component according to some embodiments of the present invention.

Figure 7A:
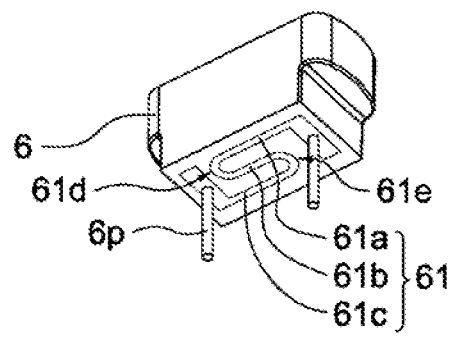
FIG. 7A, FIG. 7B, FIG. 7C and FIG. 7D are schematic diagrams of a heating component according to some embodiments of the present invention.

As shown in FIG. 7A, the heating component 6 includes a conductive component 6p and a heating circuit 61. In some embodiments, the heating circuit 61 may be disposed on a bottom surface of the heating component 6. In some embodiments, the heating circuit 61 may be exposed at the bottom surface of the heating component 6. In some embodiments, the heating circuit 61 may be disposed inside the heating component 6. In some embodiments, the heating circuit 61 may be partially covered by the heating component 6. In some embodiments, the heating circuit 61 may be completely covered by the heating component 6.

In some embodiments, the heating circuit 61 may include a section 61a, a section 61b and a section 61c.

The section 61a extends in one direction. The section 61b extends in one direction. The section 61c extends in one direction. In some embodiments, the extension direction of the section 61a may be in parallel with the extension direction of the section 61b. In some embodiments, the extension direction of the section 61a may be in parallel with the extension direction of the section 61c. In some embodiments, the extension direction of the section 61b may be in parallel with the extension direction of the section 61c.

In some embodiments, the extension direction of the section 61a may not be in parallel with the extension direction of the section 61b. In some embodiments, the extension direction of the section 61a may not be in parallel with the extension direction of the section 61c. In some embodiments, the extension direction of the section 61b may not be in parallel with the extension direction of the section 61c.

The section 61a, the section 61b and the section 61c are connected to each other. The heating circuit 61 may include connection portions 61d and 61e. The section 61a and the section 61b are connected to each other through the connection portion 61d. The section 61b and the section 61c are connected to each other through the connection portion 61e.

In some embodiments, the connection portion 61d has a curved shape. In some embodiments, the connection portion 61e has a curved shape. In some embodiments, the connection portion 61d has a curvature. In some embodiments, the connection portion 61e has a curvature. In some embodiments, the curvature of the connection portion 61d and the curvature of the connection portion 61e may be the same. In some embodiments, the curvature of the connection portion 61d and the curvature of the connection portion 61e may be different.

In some embodiments, the connection portion 61d has a concave shape facing toward one direction. In some embodiments, the connection portion 61e has a concave shape facing toward one direction. In some embodiments, the concave shape of the connection portion 61d and the concave shape of the connection portion 61e may face different directions. In some embodiments, the concave shape of the connection portion 61d and the concave shape of the connection portion 61e may face opposite directions.

The section 61a, the section 61b and the section 61c are disposed between two conductive components 6p. The connection portions 61d and 61e are disposed between the two conductive components 6p. The section 61a, the section 61b and the section 61c may increase an contact area between the heating component 6 and the heating circuit 61. The section 61a, the section 61b and the section 61c may increase heating efficiency of the heating circuit 61. In some embodiments, it is also considered that the heating circuit 61 may have more sections. In some embodiments, it is also considered that the heating circuit 61 may have fewer sections. In some embodiments, it is also considered that the heating circuit 61 may have more connection portions. In some embodiments, it is also considered that the heating circuit 61 may have fewer connection portions.

In some embodiments, the heating circuit 61 may be printed on the bottom surface of the heating component 6 by circuit printing. Manufacturing the heating circuit 61 by circuit printing may simplify a manufacturing process of the heating circuit 61. Manufacturing the heating circuit 61 by circuit printing may reduce a manufacturing cost of the heating circuit 61. In some embodiments, the heating circuit 61 may be wrapped inside the heating component 6 during a manufacturing process of the heating component 6. Damage to the heating circuit 61 in a subsequent component process may be avoided by wrapping the heating circuit 61 inside the heating component 6.

The heating circuit 61 is electrically connected to the conductive component 6p. The heating circuit 61 is physically connected to the conductive component 6p. In some embodiments, the heating circuit 61 may be directly connected to the conductive component 6p. In some embodiments, the heating circuit 61 may be indirectly connected to the conductive component 6p.

The heating circuit 61 may include a metal material. In some embodiments, the heating circuit 61 may include silver. In some embodiments, the heating circuit 61 may include platinum. In some embodiments, the heating circuit 61 may include palladium. In some embodiments, the heating circuit 61 may include a nickel alloy material.

The heating component 6 may include a ceramic material. The heating component 6 may include a diatomite material. The heating component 6 may include alumina. In some embodiments, the heating component 6 may include a semiconductive ceramic material. In some embodiments, the heating component 6 may include a heavy-doped silicon carbide. In some embodiments, the heating component 6 may include barium titanate. In some embodiments, the heating component 6 may include strontium titanate.

The heating component 6 may have a characteristic of self-limiting temperature. The resistance value of the heating component 6 rises as the temperature rises. When the temperature of the heating component 6 reaches a threshold T1, the heating component 6 has a resistance value R1. In some embodiments, when the heating component 6 reaches a threshold T1, the heating circuit 61 cannot make the temperature of the heating component 6 higher. In some embodiments, when the resistance value of the heating component 6 reaches R1, a heating power output by the heating circuit 61 cannot make the temperature of the heating component 6 higher.

In some embodiments, the threshold T1 is within a range of 200° C. to 220° C. In some embodiments, the threshold T1 is within a range of 220° C. to 240° C. In some embodiments, the threshold T1 is within a range of 240° C. to 260° C. In some embodiments, the threshold T1 is within a range of 260° C. to 280° C. In some embodiments, the threshold T1 is within a range of 280° C. to 300° C. In some embodiments, the threshold T1 is within a range of 280° C. to 300° C. In some embodiments, the threshold T2 is within a range of 300° C. to 320° C.

In some embodiments, the heating component 6 has a resistance value of over 10Ω when heated to the threshold T1. In some embodiments, the heating component 6 has a resistance value of over 15Ω when heated to the threshold T1. In some embodiments, the heating component 6 has a resistance value of over 20Ω when heated to the threshold T1. In some embodiments, the heating component 6 has a resistance value of over 30Ω when heated to the threshold T1.

The self-limiting temperature characteristic of the heating component 6 can prevent the heating component 6 from dry burning. The self-limiting temperature characteristic of the heating component 6 can reduce a chance of the vaporization device 100 from being destroyed by burning. The self-limiting temperature characteristic of the heating component 6 can increase safety of the vaporization device 100. The self-limiting temperature characteristic of the heating component 6 can increase a service life of each component in the vaporization device 100. The self-limiting temperature characteristic of the heating component 6 can effectively reduce a risk of nicotine cracking.

The self-limiting temperature characteristic of the heating component 6 can control the aerosol from the mouthpiece at a specific temperature to avoid burning lips of the user. In some embodiments, the aerosol from the mouthpiece can be controlled at a temperature of 35° C. to 40° C. In some embodiments, the aerosol from the mouthpiece can be controlled at a temperature of 40° C. to 45° C. In some embodiments, the aerosol from the mouthpiece can be controlled at a temperature of 45° C. to 50° C. In some embodiments, the aerosol from the mouthpiece can be controlled at a temperature of 50° C. to 55° C. In some embodiments, the aerosol from the mouthpiece can be controlled at a temperature of 55° C. to 60° C. In some embodiments, the aerosol from the mouthpiece can be controlled at a temperature of 60° C. to 65° C.

Figure 7B:
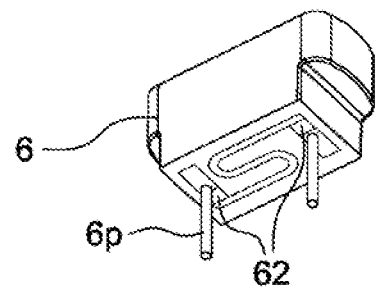

As shown in FIG. 7B, the heating circuit 61 may be indirectly connected to the conductive component 6p. In some embodiments, a protection component 62 may be disposed between the heating circuit 61 and the conductive component 6p.

In some embodiments, the protection component 62 is resettable.

The protection component 62 forms an open circuit when the temperature of the protection component 62 reaches a threshold T2. The protection component 62 forms a short circuit when the temperature of the protection component 62 drops to a threshold T3. The conductive component 6p cannot provide a current for the heating circuit 61 when the temperature of the protection component 62 reaches the threshold T2. The conductive component 6p provides a current for the heating circuit 61 when the temperature of the protection component 62 drops to the threshold T3.

In some embodiments, the threshold T3 and the threshold T2 may be the same. In some embodiments, the threshold T3 and the threshold T2 may be different. In some embodiments, the threshold T3 may be less than the threshold T2.

In some embodiments, the threshold T2 is within a range of 200° C. to 220° C. In some embodiments, the threshold T2 is within a range of 220° C. to 240° C. In some embodiments, the threshold T2 is within a range of 240° C. to 260° C. In some embodiments, the threshold T2 is within a range of 260° C. to 280° C. In some embodiments, the threshold T2 is within a range of 280° C. to 300° C. In some embodiments, the threshold T2 is within a range of 300° C. to 320° C.

In some embodiments, the threshold T3 is within a range of 180° C. to 200° C. In some embodiments, the threshold T3 is within a range of 200° C. to 220° C. In some embodiments, the threshold T3 is within a range of 220° C. to 240° C. In some embodiments, the threshold T3 is within a range of 240° C. to 260° C. In some embodiments, the threshold T3 is within a range of 260° C. to 280° C. In some embodiments, the threshold T3 is within a range of 280° C. to 300° C. In some embodiments, the protection component 62 may be a resettable fuse.

In some embodiments, the protection component 62 is non-resettable.

The protection component 62 forms an open circuit (open circuit) when the temperature of the protection component 62 reaches a threshold T2. In some embodiments, the protection component 62 that forms an open circuit dose not form a short circuit as the temperature drops.

The protection component 62 may prevent the heating component 6 from dry burning. The protection component 62 may reduce the chance of the vaporization device 100 being destroyed by burning. The protection component 62 may increase the safety of the vaporization device 100. The protection component 62 may increase the service life of each component in the vaporization device 100.

Figures 7C, 7D:
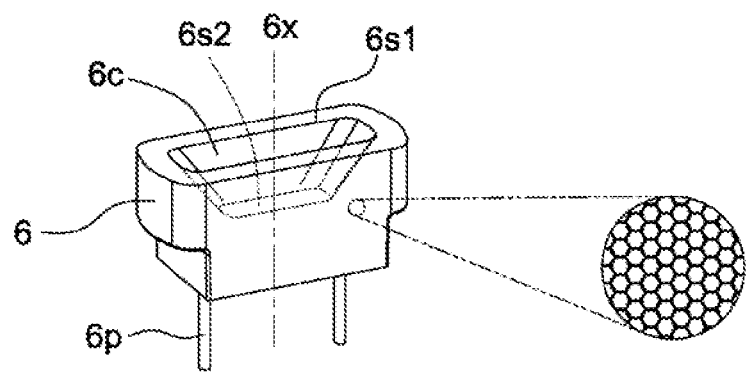

As shown in FIG. 7C, the heating component 6 has an axisymmetric shape relative to an axis 6x. In some embodiments, the heating component 6 has an asymmetric shape. A top surface of the heating component 6 may be provided with a groove 6c. The groove 6c may have an axisymmetric shape relative to the axis 6x. In some embodiments, the groove 6c may have an asymmetric shape.

The heating component 6 is disposed between the heating component top cap 4 and the heating component base 8. When the heating component 6 is disposed between the heating component top cap 4 and the heating component base 8 as shown in FIG. 6E, the through hole 4h1 and the axis 6x do not overlap. When the heating component 6 is disposed between the heating component top cap 4 and the heating component base 8 as shown in FIG. 6E, the through hole 4h2 and the axis 6x do not overlap. When the heating component 6 is disposed between the heating component top cap 4 and the heating component base 8 as shown in FIG. 6E, an extension direction of the axis 6x does not pass through the through hole 4h1. When the heating component 6 is disposed between the heating component top cap 4 and the heating component base 8 as shown in FIG. 6E, the extension direction of the axis 6x does not pass through the through hole 4h2.

Referring to FIG. 3B again, the extension direction of the axis 6x does not pass through the air inlet channel 31 when the heating component 6 is disposed inside the cartridge 100A. The extension direction of the axis 6x and the extension direction of the air inlet channel 31 do not overlap. The extension direction of the axis 6x passes through the through hole 1h when the heating component 6 is disposed inside the cartridge 100A. The extension direction of the axis 6x passes through a portion of the air outlet channel 32 close to the through hole 1h when the heating component 6 is disposed inside the cartridge 100A. The extension direction of the axis 6x does not pass through another part of the air outlet channel 32 away from the through hole 1h when the heating component 6 is disposed inside the cartridge 100A.

The vaporizable material makes direct contact with the heating component 6 via an inner wall of the groove 6c. The groove 6c may have an opening 6s1. The groove 6c may have a bottom surface 6s2. In some embodiments, the area of the opening 6s1 and the area of the bottom surface 6s2 may be the same. In some embodiments, the area of the opening 6s1 and the area of the bottom surface 6s2 may be different. In some embodiments, the area of the opening 6s1 may be larger than the area of the bottom surface 6s2. The groove 6c of the heating component 6 may increase a contact area between the heating component 6 and the e-liquid.

FIG. 7D shows an enlarged view of a portion of the heating component 6. As shown in FIG. 7D, the heating component 6 may have pores. In some embodiments, a shape of the pores may be square. In some embodiments, a shape of the pores may be cylindrical. In some embodiments, a shape of the pores may be a ring. In some embodiments, a shape of the pores may be a hexagonal column. In some embodiments, a shape of the pores may be a honeycomb structure.

The e-liquid can permeate into the pores of the heating component 6. The pores of the heating component 6 can be infiltrated in the e-liquid. The pores of the heating component 6 may increase the contact area between the heating component 6 and the e-liquid. The pores of the heating component 6 can surround small molecules of the e-liquid from all sides. During the heating process, the pores of the heating component 6 allows the e-liquid to be more uniformly heated. During the heating process, the pores of the heating component 6 allows the e-liquid to faster reach a predetermined temperature. During the heating process, the pores of the heating component 6 can prevent the burnt odor.

In some embodiments, the heating component 6 has a porosity of 20% to 30%. In some embodiments, the heating component 6 has a porosity of 30% to 40%. In some embodiments, the heating component 6 has a porosity of 40% to 50%. In some embodiments, the heating component 6 has a porosity of 50% to 60%. In some embodiments, the heating component 6 has a porosity of 60% to 70%. In some embodiments, the heating component 6 has a porosity of 70% to 80%.

In some embodiments, the heating component 6 has a specific quantity of closed pores. In some embodiments, the closed pores may include alumina. In some embodiments, the closed pores may include silicon carbide. In some embodiments, the heating component 6 has a closed porosity of 10% to 20%. In some embodiments, the heating component 6 has a closed porosity of 20% to 30%. In some embodiments, the heating component 6 has a closed porosity of 30% to 40%.

Figure 8A:
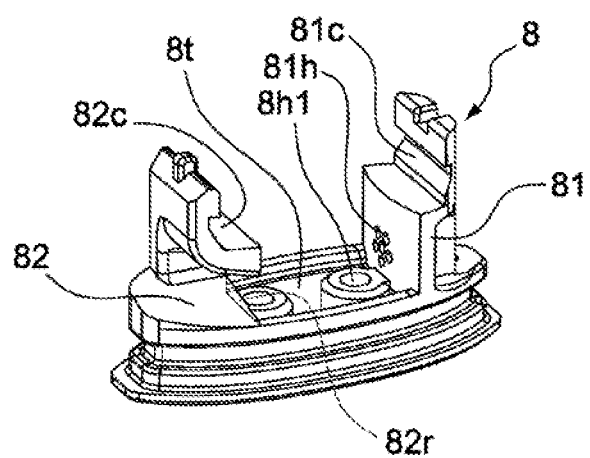
FIG. 8A, FIG. 8B and FIG. 8C are schematic diagrams of a heating component base according to some embodiments of the present invention.
Figure 8B:
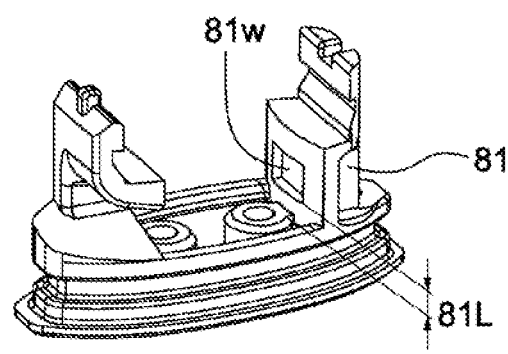
Figure 8C:
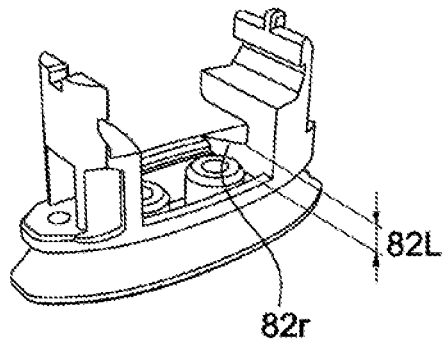

FIG. 8A, FIG. 8B and FIG. 8C are schematic diagrams of a heating component base according to some embodiments of the present invention.

As shown in FIG. 8A, the heating component base 8 includes a supporting member 81 and a supporting member 82. The supporting member 81 is disposed next to the air inlet channel 31. The supporting member 82 is disposed next to the air outlet channel 32. The supporting member 81 has a buckle part 81c. The supporting member 82 has a buckle part 82c. The heating component base 8 is combined with the heating component top cap 4 via the buckle parts 81c and 82c. The heating component base 8 is removably combined with the heating component top cap 4 via the buckle parts 81c and 82c. The heating component 6 is disposed between the heating component top cap 4 and the heating component base 8.

The supporting member 81 may have one or more through holes 81h. In some embodiments, the supporting member 81 may have 6 through hole 81h. The through holes 81h penetrate the supporting member 81. The through holes 81h allows the vaporization chamber 8c and the air inlet channel 31 to be in communication with each other. The aperture area of the through holes 81h is designed to allow air to pass through. The arrangement of the through holes 81h is designed to allow air to pass through.

The aperture area of the through holes 81h is designed to make it difficult for the e-liquid to pass through. The arrangement of the through holes 81h is designed to make it difficult for the e-liquid to pass through. In some embodiments, the diameter of each of the through holes 81h is within a range of 0.2 mm to 0.3 mm. In some embodiments, the diameter of each of the through holes 81h is within a range of 0.3 mm to 0.4 mm. In some embodiments, the diameter of each of the through holes 81h is within a range of 0.4 mm to 0.5 mm. In some embodiments, the diameter of each of the through holes 81h is within a range of 0.5 mm to 0.6 mm. In some embodiments, the diameter of each of the through holes 81h is within a range of 0.6 mm to 0.7 mm. In some embodiments, each of the through holes 81h may have a diameter of 0.55 mm.

A bottom of the supporting member 82 close to the heating component base 8 has a ramp structure 82r. One end of a cross section of the ramp structure 82r has a height of 82L. The height 82L may be a largest distance between the ramp structure 82r and the e-liquid tank 8t. In some embodiments, the ramp structure 82r may be replaced with a staircase structure. Both ends of a cross section of the staircase structure may have a substantially same height. The ramp structure 82r may form a block portion of the e-liquid tank 8t.

When the user is inhaling, the ramp structure 82r may prevent the e-liquid or liquid stored in the e-liquid tank 8t from entering the air outlet channel 32. When the user is inhaling, the staircase structure 82r may prevent the e-liquid or liquid stored in the e-liquid tank 8t from entering the air outlet channel 32.

In some embodiments, a bottom of the e-liquid tank 8t may be provided with an e-liquid adsorbing cotton (not shown). The e-liquid adsorbing cotton may adsorb the e-liquid or liquid stored in the e-liquid tank 8t. The e-liquid or liquid adsorbed by the e-liquid adsorbing cotton is less likely to flow in the e-liquid tank 8t.

As shown in FIG. 8B, the supporting member 81 may have a window 81w. The window 81w may be an opening. The window 81w penetrates the supporting member 81. The window 81w allows the vaporization chamber 8c and the air inlet channel 31 to be in communication with each other. The aperture area of the window 81w is designed to allow air to pass through. A height 81L is provided between the window 81w and the e-liquid tank 8t. The height 81L may prevent the e-liquid or liquid stored in the e-liquid tank 8t from entering the air inlet channel 31. In some embodiments, the height 81L is within a range of 1 mm to 2 mm. In some embodiments, the height 81L is within a range of 2 mm to 3 mm. In some embodiments, the height 81L is within a range of 3 mm to 4 mm. In some embodiments, the height 81L is within a range of 4 mm to 5 mm.

The height 81L may form a block portion of the e-liquid tank 8t. Referring to FIG. 8A again, the minimum height between the one or more through holes 81h and the e-liquid tank 8t may be equal to 81L. Referring to FIG. 8A again, the minimum height between the one or more through holes 81h and the e-liquid tank 8t may be different from 81L. In some embodiments, the minimum height between the one or more through holes 81h and the e-liquid tank 8t may be larger than 81L.

As shown in FIG. 8C, a height 82L is provided between the ramp structure 82r and the bottom of the e-liquid tank 8t. In some embodiments, the height 82L is within a range of 1 mm to 2 mm. In some embodiments, the height 82L is within a range of 2 mm to 3 mm. In some embodiments, the height 82L is within a range of 3 mm to 4 mm. In some embodiments, the height 82L is within a range of 4 mm to 5 mm.

Figure 8D:
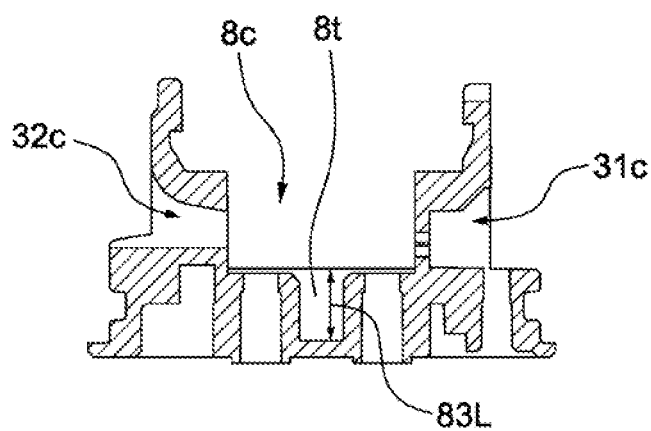
FIG. 8D is a sectional view of a heating component base according to some embodiments of the present invention.

FIG. 8D is a sectional view of a heating component base according to some embodiments of the present invention. The e-liquid tank 8t has a depth 83L. The depth 83L may be less than the height 81L. The depth 83L may be less than the height 82L. The depth 83L may be equal to the height 82L. The air inlet channel 31 is in communication with the vaporization chamber 8c through the communication portion 31c. The air outlet channel 32 is in communication with the vaporization chamber 8c through the communication portion 32c.

Figure 9A:
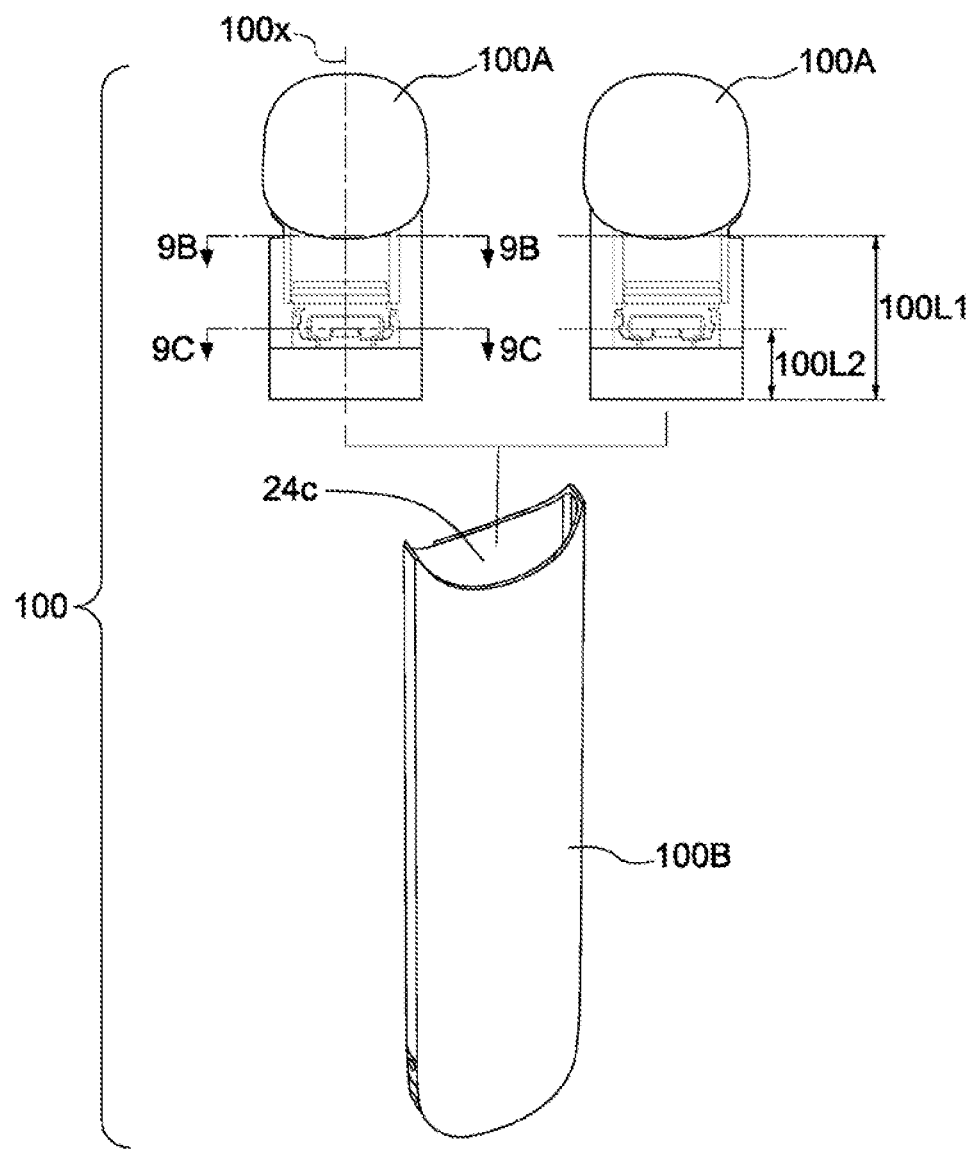
FIG. 9A is a schematic diagram of a vaporization device combination according to some embodiments of the present invention.

FIG. 9A is a schematic diagram of a vaporization device combination according to some embodiments of the present invention. The vaporization device 100 may include a cartridge 100A and a body 100B. The cartridge 100A may be designed to be removably combined with the body 100B. The body 100B may have an accommodation portion 24c. A portion of the cartridge 100A may be stored in the accommodation portion 24c. The accommodation portion 24c may surround a portion of the cartridge 100A. The accommodation portion 24c may wrap a portion of the cartridge 100A. A portion of the cartridge 100A may be exposed by the body 100B.

The cartridge 100A may be removably combined with the body 100B in two directions. In some embodiments, the air inlet channel 31 may face towards a left side of the cartridge 100A when the cartridge 100A and the body 100B are combined. In some embodiments, the air inlet channel 31 may face towards a right side of the cartridge 100A when the cartridge 100A and the body 100B are combined. In the foregoing situations, the vaporization device 100 can work normally no matter in which direction the cartridge 100A is combined with the body 100B.

When the cartridge 100A is combined with the body 100B in a first direction (for example, the air inlet channel 31 may face towards the left side of the cartridge 100A), the conductive contact 9 of the cartridge 100A and the conductive probe 15 of the body 100B make contact with each other. When the cartridge 100A is combined with the body 100B in the first direction, the conductive contact 9 of the cartridge 100A and the conductive probe 15 of the body 100B are electrically connected to each other. When the cartridge 100A is combined with the body 100B in a second direction (for example, the air inlet channel 31 may face towards the right side of the cartridge 100A), the conductive contact 9 of the cartridge 100A and the conductive probe 15 of the body 100B make contact with each other. When the cartridge 100A is combined with the body 100B in the second direction, the conductive contact 9 of the cartridge 100A and the conductive probe 15 of the body 100B are electrically connected to each other.

Figure 9B:
FIG. 9B and FIG. 9C are sectional views of a cartridge according to some embodiments of the present invention.
Figure 9C:

FIG. 9B and FIG. 9C are sectional views of a cartridge according to some embodiments of the present invention.

A cross section 3s1 of the cartridge 100A at a length 100L1 from the lower surface 11s of the metal base 11 is shown in FIG. 9B. A cross section 3s2 of the cartridge 100A at a length 100L2 from the lower surface 11s of the metal base 11 is shown in FIG. 9C. As shown in FIG. 9B, the cartridge housing 3 may have an asymmetrical cross section 3s1 at a length 100L1 from the lower surface 11s of the metal base 11. As shown in FIG. 9C, the cartridge housing 3 may have an asymmetrical cross section 3s2 at a length 100L2 from the lower surface 11s of the metal base 11. In some embodiments, the cross section 3s1 is non-axisymmetric relative to an axis 100x. In some embodiments, the cross section 3s2 is non-axisymmetric relative to the axis 100x. As shown in FIG. 9A, the axis 100x extends from a top of the cartridge 100A to a bottom.

When the cartridge 100A is removably combined with the body 100B, the accommodation portion 24c wraps the cross section 3s1. When the cartridge 100A is removably combined with the body 100B, the accommodation portion 24c wraps the cross section 3s2.

Figure 10:
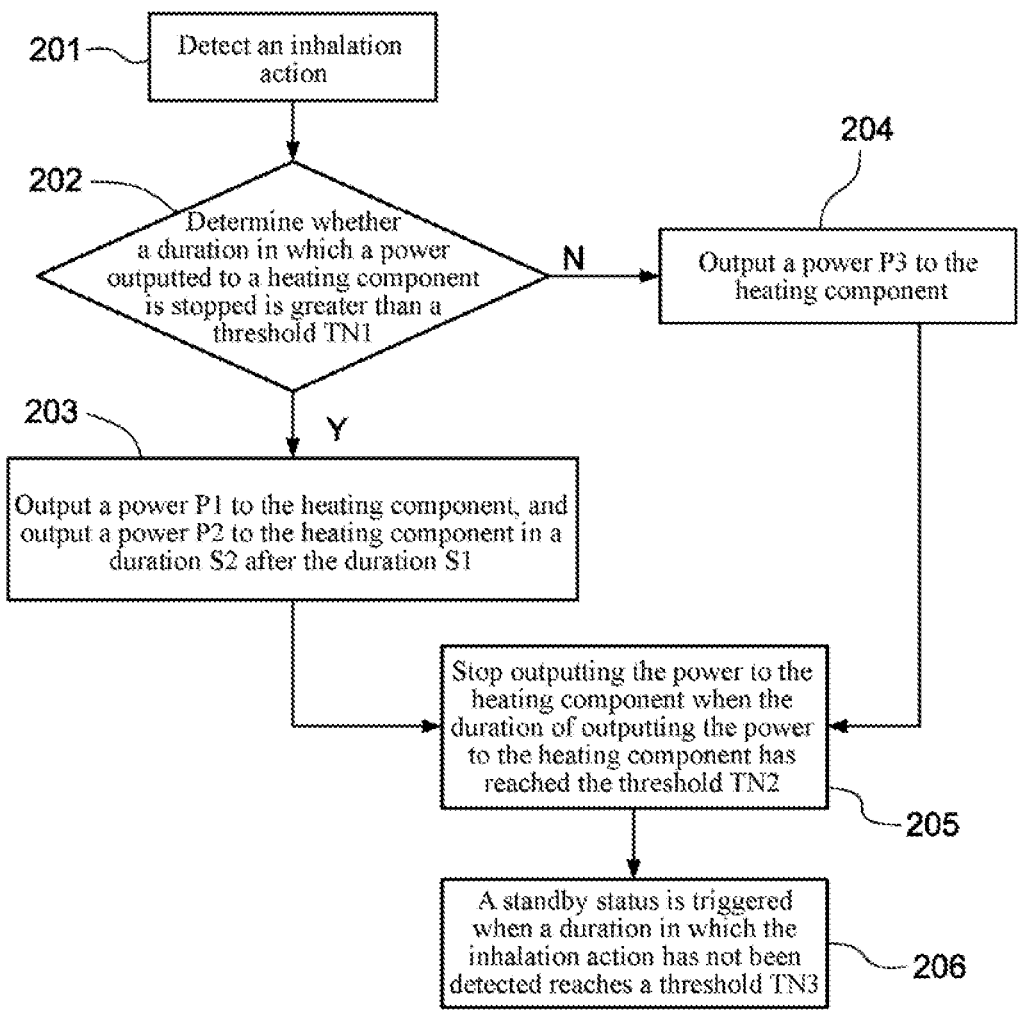
FIG. 10 is a flowchart of an output power control method according to some embodiments of the present invention.

FIG. 10 is a flowchart of an output power control method according to some embodiments of the present invention.

The output power control method 200 may include a plurality of steps. In some embodiments, the steps in the output power control method 200 may be performed sequentially in the order shown in FIG. 10. In some embodiments, the steps in the output power control method 200 may not be performed in the order shown in FIG. 10.

Step 201: Detect an inhalation action of the user. The Step 201 may be performed by a sensor 16 and a controller 171 in combination.

Step 202: Determine whether a duration in which a power outputted to the heating component 6 is stopped is greater than a threshold TN1. If the time when an output power to the heating component 6 is stopped is greater than or equal to the threshold TN1, Step 203 is performed. If the time when an output power to the heating component 6 is stopped is less than the threshold TN1, Step 204 is performed. Step 202 may be performed by setting a timer in the controller 171. A timer may be set in the controller 171, and starts when the power supply component 20 stops provide power for the heating component 6.

In some embodiments, the threshold TN1 is within a range of 15 seconds to 60 seconds. In some embodiments, the threshold TN1 is within a range of 25 seconds to 40 seconds. In some embodiments, the threshold TN1 may be 30 seconds.

Step 203: Output a power P1 to the heating component 6 in a duration S1, and output a power P2 to the heating component 6 in a duration S2 after the duration S1. The duration S1 and the duration S2 are both during the continuous inhalation action of the user. Step 204 may be performed by the controller 171, a circuit board 17, a power supply component 20, a conductive contact 9, a conductive probe 15 and the heating component 6 in combination.

In some embodiments, the power P1 may be greater than the power P2. In some embodiments, P1 is within a range of 6 W to 15 W. In some embodiments, P1 is within a range of 7.2 W to 9 W. In some embodiments, P2 is within a range of 4.5 W to 9 W. In some embodiments, P2 is within a range of 6 W to 8 W.

In some embodiments, S1 is within a range of 0.1 second to 2 seconds. In some embodiments, S1 is within a range of 0.1 second to 1 seconds. In some embodiments, S1 is within a range of 0.1 second to 0.6 seconds.

In some embodiments, S2 is within a range of 0.1 second to 4 seconds. In some embodiments, S2 is within a range of 0.1 second to 3.5 seconds.

Step 202 and Step 203 have a plurality of advantages. Whether the vaporization device 100 has not been in use for a long time can be determined by the threshold TN1. The heating component 6 appears in a cool state when the user has not used the vaporization device 100 for a long time. When the user performs a first inhalation action to the vaporization device 100, the vaporization device 100 may output a relative high power P1 in the duration S1. The relative high power P1 may accelerate the generation of an aerosol. When the inhalation action of the user lasts for the duration S2, the heating component 6 already has a specific temperature, and the vaporization device 100 can reduce the output power to P2. The reduced power P2 may allow the aerosol to be generated uniformly. The reduced power P2 may increase the use time of the power supply component 20.

Step 204: Output a power P3 to the heating component. Step 203 may be performed by the controller 171, the circuit board 17, the power supply component 20, the conductive contact 9, the conductive probe 15 and the heating component 6 in combination.

In some embodiments, P3 is within a range of 3.5 W to 10 W. In some embodiments, P3 is within a range of 4.5 W to 9 W. In some embodiments, P3 is within a range of 6 W to 8 W. In some embodiments, P3 and P2 may be the same. In some embodiments, P3 and P2 may be different.

Step 202 and Step 204 have a plurality of advantages. Whether the vaporization device 100 has been used by the user in a short time can be determined by the threshold TN1. If the vaporization device 100 has been used by the user in a short time, the heating component 6 has not been cooled completely. If the vaporization device 100 has been used by the user in a short time, the heating component 6 has a specific temperature. In this case, the vaporization device 100 may adjust the output power to P3. The adjusted power P3 allows the aerosol to be generated uniformly. The adjusted power P3 may increase the use time of the power supply component 20.

Step 205: Stop outputting the power to the heating component when the duration of outputting the power to the heating component has reached the threshold TN2. Step 205 may be performed by setting a timer in the controller 171.

Step 205 has many advantages. When the time of the heating component 6 being continuously heated has reached the threshold TN2, the stop of heating may prevent the heating component 6 from being overheated. Overheated heating component 6 may damage another component inside the vaporization device 100. Overheated heating component 6 may decrease service lives of components inside the vaporization device 100. When the time of the heating component 6 being continuously heated has reached the threshold TN2, the stop of heating may prevent the heating component 6 from dry burning. Drying burning the heating component 6 may produce a burnt odor. Drying burning the heating component 6 may produce toxic chemicals.

In some embodiments, the threshold TN2 is within a range of 2 seconds to 10 seconds.

Step 206: The vaporization device 100 is triggered to enter a standby state when a duration in which the inhalation action has not been detected reaches a threshold TN3. When staying in the standby state, the power consumption of the vaporization device 100 is reduced. When staying in the standby state, the sensor 16 remains in an active state. Step 206 may be performed by setting a timer in the controller 171.

When the user stops inhaling, the output power control method 200 may further include a step of stopping outputting power to the heating component 6. The step may be performed by the sensor 16 and the controller 171 in combination.

As used herein, space-related terms such as "under", "below", "lower portion", "above", "upper portion", "lower portion", "left side", "right side", and the like may be used herein to simply describe a relationship between one element or feature and another element or feature as shown in the figures. In addition to orientation shown in the figures, space-related terms are intended to encompass different orientations of the device in use or operation. An apparatus may be oriented in other ways (rotated 90 degrees or at other orientations), and the space-related descriptors used herein may also be used for explanation accordingly. It should be understood that when an element is "connected" or "coupled" to another element, the element may be directly connected to coupled to another element, or an intermediate element may exist.

As used herein, the terms "approximately", "basically", "substantially", and "about" are used to describe and explain small variations. When used in combination with an event or a situation, the terms may refer to an example in which an event or a situation occurs accurately and an example in which the event or situation occurs approximately. As used herein with respect to a given value or range, the term "about" generally means in the range of ±10%, ±5%, ±1%, or ±0.5% of the given value or range. The range may be indicated herein as from one endpoint to another endpoint or between two endpoints. Unless otherwise specified, all ranges disclosed herein include endpoints. The term "substantially coplanar" may refer to two surfaces within a few micrometers (μm) positioned along the same plane, for example, within 10 μm, within 5 μm, within 1 μm, or within 0.5 μm located along the same plane. When reference is made to "substantially" the same numerical value or characteristic, the term may refer to a value within ±10%, ±5%, ±1%, or ±0.5% of the average of the values.

As used herein, the terms "approximately", "basically", "substantially", and "about" are used to describe and explain small variations. When used in combination with an event or a situation, the terms may refer to an example in which an event or a situation occurs accurately and an example in which the event or situation occurs approximately. For example, when being used in combination with a value, the term may refer to a variation range of less than or equal to ±10% of the value, for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, if a difference between two values is less than or equal to ±10% of an average value of the value (for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%), it could be considered that the two values are "substantially" the same. For example, being "substantially" parallel may refer to an angular variation range of less than or equal to ±10° with respect to 0°, for example, less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°. For example, being "substantially" perpendicular may refer to an angular variation range of less than or equal to ±10° with respect to 90°, for example, less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

As used herein, singular terms "a", "an", and "said" may include plural referents unless the context clearly dictates otherwise. In the description of some embodiments, assemblies provided "on" or "above" another component may encompass a case in which a previous component is directly on a latter component (for example, in physical contact with the latter component), and a case in which one or more intermediate assemblies are located between the previous component and the latter component.

Unless otherwise specified, space descriptions such as "above", "below", "up", "left", "right", "down", "top portion", "bottom portion", "vertical", "horizontal", "side face", "higher than", "lower than", "upper portion", "on", "under", "downward", etc. are indicated relative to the orientation shown in the figures. It should be understood that the space descriptions used herein are merely for illustrative purposes, and actual implementations of the structures described herein may be spatially arranged in any orientation or manner, provided that the advantages of embodiments of the present invention are not deviated due to such arrangement.

Although the illustrative embodiments have been shown and described, it should be understood by those skilled in the art that the above embodiments cannot be interpreted as limitations to the present application, and the embodiments can be changed, substituted and modified without departing from the spirit, principle and scope of the present application.

What is claimed is:

1. An vaporization device, comprising:
   a cartridge, having a housing, a heating component and a heating component base, wherein
      the housing and the heating component base define an air inlet channel and an air outlet channel, and the heating component and the heating component base define a cavity there between; and
      the air inlet channel is in communication with the cavity through a first communication portion, the air outlet channel is in communication with the cavity through a second communication portion, and the first communication portion and the second communication portion are located between the heating component and the heating component base; and
   a body, having an accommodation portion, wherein
   when the cartridge and the body are removably combined, the accommodation portion covers a portion of the cartridge;
   wherein the vaporization device further comprises a hollow tube disposed on the heating component base, the hollow tube extending from the heating component base into the air inlet channel.

2. The vaporization device according to claim 1, wherein a first through hole in communication with the air inlet channel and a second through hole in communication with the air outlet channel are disposed on the housing, and the distance between the first through hole and the heating component is less than the distance between the second through hole and the heating component.

3. The vaporization device according to claim 1, wherein the air inlet channel extends in a first direction, the first communication portion extends in a second direction, and the first direction is different from the second direction.

4. The vaporization device according to claim 1, wherein the air outlet channel extends in a first direction, the second communication portion extends in a second direction, and the first direction is different from the second direction.

5. The vaporization device according to claim 1, wherein the air outlet channel has a first portion extending in a first direction and a second portion extending in a second direction, and the first direction is different from the second direction.

6. The vaporization device according to claim 1, wherein the heating component base wraps a first portion of the hollow tube and exposes a second portion of the hollow tube, and the second portion is not in contact with the housing.

7. The vaporization device according to claim 1, wherein the air inlet channel is located on a first side of the heating component, and the air outlet channel is located on a second side of the heating component opposite to the first side.

8. A device configured to store a solution, comprising:
   a housing, a heating component, a heating component top cap and a heating component base, wherein
   the housing and the heating component top cap define a storage compartment, and the storage compartment is in fluid communication with the heating component;
   the housing and the heating component base define an air inlet channel and an air outlet channel, and the heating component and the heating component base define a cavity there between; and
   the air inlet channel is in communication with the cavity through a first communication portion, the air outlet channel is in communication with the cavity through a second communication portion, and the first communication portion and the second communication portion are located between the heating component and the heating component base;
   wherein the device further comprises a hollow tube disposed on the heating component base, the hollow tube extending from the heating component base into the air inlet channel.

9. The device according to claim 8, wherein the heating component base has a supporting member, and the air outlet channel is in communication with the cavity through an opening on the supporting member.

10. The device according to claim 8, wherein the heating component is configured to heat the solution stored in the storage compartment to generate an aerosol in the cavity.

11. The device according to claim 8, wherein a first through hole in communication with the air inlet channel is disposed on the housing, and the heating component is between the first through hole and the first communication portion in a first direction.

12. The device according to claim 11, wherein the housing has a second through hole in communication with the air outlet channel, and the heating component is between the second through hole and the second communication portion in the first direction.

13. The device according to claim 8, further comprising a heating circuit disposed on a surface of the heating component, the heating circuit having a first section, a second section and a third section.

14. The device according to claim 13, wherein the first section is in parallel with the second section, and the second section is in parallel with the third section.

15. The device according to claim 13, wherein the first section is connected to the second section through a first connection portion, and the second section is connected to the third section through a second connection portion.

16. The device according to claim 15, wherein the first connection portion has a concave shape facing toward a first direction, the second connection portion has a concave shape facing toward a second direction, and the first direction is different from the second direction.

17. A method for operating a vaporization device, comprising:
   causing a first airflow to enter, along an air inlet channel, a cavity between a heating component and a heating component base through a first through hole of a housing, wherein the air inlet channel is defined by the housing and the heating component base;

causing the first airflow to enter an air outlet channel from the cavity, wherein the air outlet channel is defined by the housing and the heating component base; and causing the first airflow to leave, through a second through hole on the housing, the cavity along the air outlet channel, wherein the first airflow experiences a first direction change when entering the cavity from the air inlet channel, and experiences a second direction change when entering the air outlet channel from the cavity;

wherein the method further comprises causing a second airflow to enter the air inlet channel through a hollow tube disposed on the heating component base.

18. The method according to claim 17, wherein the first airflow experiences a third direction change when approaching the second through hole, and experiences a fourth direction change when entering the second through hole.

19. The method according to claim 17, further comprising causing the first airflow to pass through one or more through holes on a supporting member of the heating component base when entering the air outlet channel from the cavity.

* * * * *